(12) United States Patent
Carter et al.

(10) Patent No.: US 9,486,557 B2
(45) Date of Patent: *Nov. 8, 2016

(54) DEMINERALIZED BONE FIBERS HAVING CONTROLLED GEOMETRY AND SHAPES AND METHODS THEREOF

(71) Applicant: THERACELL, INC., Northridge, CA (US)

(72) Inventors: Andrew J. Carter, Stow, MA (US); Nelson L. Scarborough, Andover, MA (US); Bradley Patt, Northridge, CA (US)

(73) Assignee: THERACELL, INC., Northridge, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/567,788

(22) Filed: Dec. 11, 2014

(65) Prior Publication Data

US 2015/0093429 A1 Apr. 2, 2015

Related U.S. Application Data

(63) Continuation of application No. 14/256,911, filed on Apr. 18, 2014.

(60) Provisional application No. 61/814,192, filed on Apr. 19, 2013, provisional application No. 61/864,499, filed on Aug. 9, 2013, provisional application No. 61/952,128, filed on Mar. 12, 2014.

(51) Int. Cl.
*A61L 27/38* (2006.01)
*A61L 27/36* (2006.01)
*A61L 27/54* (2006.01)

(52) U.S. Cl.
CPC .......... *A61L 27/3847* (2013.01); *A61L 27/365* (2013.01); *A61L 27/3608* (2013.01);
(Continued)

(58) Field of Classification Search
CPC ........... A61L 27/3847; A61L 27/3608; A61L 27/365; A61L 27/54; A61L 27/3687; A61L 2530/02; A61L 2430/40; A61L 2400/06
See application file for complete search history.

(56) References Cited

U.S. PATENT DOCUMENTS 4,877,864 A 10/1989 Wang et al.
5,013,649 A 5/1991 Wang et al.
(Continued)

FOREIGN PATENT DOCUMENTS

WO WO 93/00432 1/1993
WO WO 94/26892 11/1994
WO WO 94/26893 11/1994

OTHER PUBLICATIONS

International Search Report and Written Opinion for corresponding PCT application No. PCT/US14/34732, mailed Sep. 25, 2014, 10pp.
(Continued)

*Primary Examiner* — Trevor Love
(74) *Attorney, Agent, or Firm* — Lewis Roca Rothgerber Christie LLP

(57) ABSTRACT

A bone repair composition and methods thereof include elongated bone fibers made from cortical bone in which a plurality of approximately uniform bone fibers is made into various implant shapes conducive for various applications. The bone fiber compositions may be in the form of a cavity, ball, pellet, wrap, strip, cylinder, cone, putty, gel, or injectable slurry.

17 Claims, 25 Drawing Sheets

(52) U.S. Cl.
CPC ............ *A61L27/3687* (2013.01); *A61L 27/54* (2013.01); *A61L 2400/06* (2013.01); *A61L 2430/02* (2013.01); *A61L 2430/40* (2013.01)

(56) References Cited

U.S. PATENT DOCUMENTS

| | | | |
|---|---|---|---|
| 5,106,748 | A | 4/1992 | Wozney et al. |
| 5,108,922 | A | 4/1992 | Wang et al. |
| 5,116,738 | A | 5/1992 | Wang et al. |
| 5,298,254 | A | 3/1994 | Prewett et al. |
| 5,366,875 | A | 11/1994 | Wozney et al. |
| 5,507,813 | A | 4/1996 | Dowd et al. |
| 5,607,269 | A | 3/1997 | Dowd et al. |
| 6,436,138 | B1 | 8/2002 | Dowd et al. |
| 6,458,375 | B1 | 10/2002 | Gertzman et al. |
| 6,504,079 | B2 | 1/2003 | Tucker et al. |
| 6,616,698 | B2 | 9/2003 | Scarborough |
| 6,630,153 | B2 | 10/2003 | Long et al. |
| 6,696,073 | B2 | 2/2004 | Boyce et al. |
| 7,163,691 | B2 | 1/2007 | Knaack et al. |
| 7,323,193 | B2 | 1/2008 | Morris et al. |
| 7,582,309 | B2 | 9/2009 | Rosenberg et al. |
| 7,608,113 | B2 | 10/2009 | Boyer, II et al. |
| 7,744,597 | B2 | 6/2010 | Gaskins et al. |
| 7,959,941 | B2 | 6/2011 | Knaack et al. |
| 8,133,421 | B2 | 3/2012 | Boyce et al. |
| 8,202,539 | B2 | 6/2012 | Behnam et al. |
| 8,268,008 | B2 | 9/2012 | Betz et al. |
| 8,333,985 | B2 | 12/2012 | Knaack et al. |
| 8,357,384 | B2 | 1/2013 | Behnam et al. |
| 2003/0055511 | A1 | 3/2003 | Schryver et al. |
| 2004/0019132 | A1 | 1/2004 | Long et al. |
| 2005/0251267 | A1 | 11/2005 | Winterbottom et al. |
| 2005/0283255 | A1 | 12/2005 | Geremakis et al. |
| 2008/0058953 | A1 | 3/2008 | Scarborough |
| 2008/0305145 | A1 | 12/2008 | Shelby et al. |
| 2010/0036503 | A1 | 2/2010 | Chen et al. |
| 2011/0045044 | A1 | 2/2011 | Masinaei et al. |
| 2011/0070312 | A1 | 3/2011 | Wei et al. |
| 2011/0076771 | A1 | 3/2011 | Gabriele et al. |
| 2012/0053692 | A1 | 3/2012 | Voor et al. |
| 2012/0082704 | A1 | 4/2012 | Phillips et al. |
| 2012/0116515 | A1 | 5/2012 | Semler et al. |
| 2012/0195971 | A1 | 8/2012 | Missos et al. |
| 2012/0251609 | A1 | 10/2012 | Huang et al. |
| 2012/0258178 | A1 | 10/2012 | Benham et al. |
| 2013/0013071 | A1 | 1/2013 | Betz et al. |
| 2013/0136777 | A1 | 5/2013 | Behnam et al. |
| 2013/0189338 | A1* | 7/2013 | Drapeau ............ A61L 27/3608 424/402 |

OTHER PUBLICATIONS

Das, Dipayan et al.; "An Investigation into Fiber Dispersion Behavior in Water with Reference to Wet-Lay Nonwoven Technology"; Journal of Dispersion Science and Technology; 33; 2012; pp. 1225-1232.

Martin, George J. et al.; "New Formulations of Demineralized Bone Matrix as a More Effective Graft Alternative in Experimental Posterolateral Lumbar Spine Arthrodesis"; Spine; vol. 24; No. 7; 1999; pp. 637-645.

Pietrzak, William S. et al.; "BMP depletion occurs during prolonged acid demineralization of bone: characterization and implications for graft preparation"; Cell Tissue Bank; Dec. 29, 2009; 8pp.

Turbak, Albin F.; "Nonwovens: Theory, Process, Performance, and Testing"; 1993; Chapter 6; ISBN: 089852265X; 28pp.

* cited by examiner

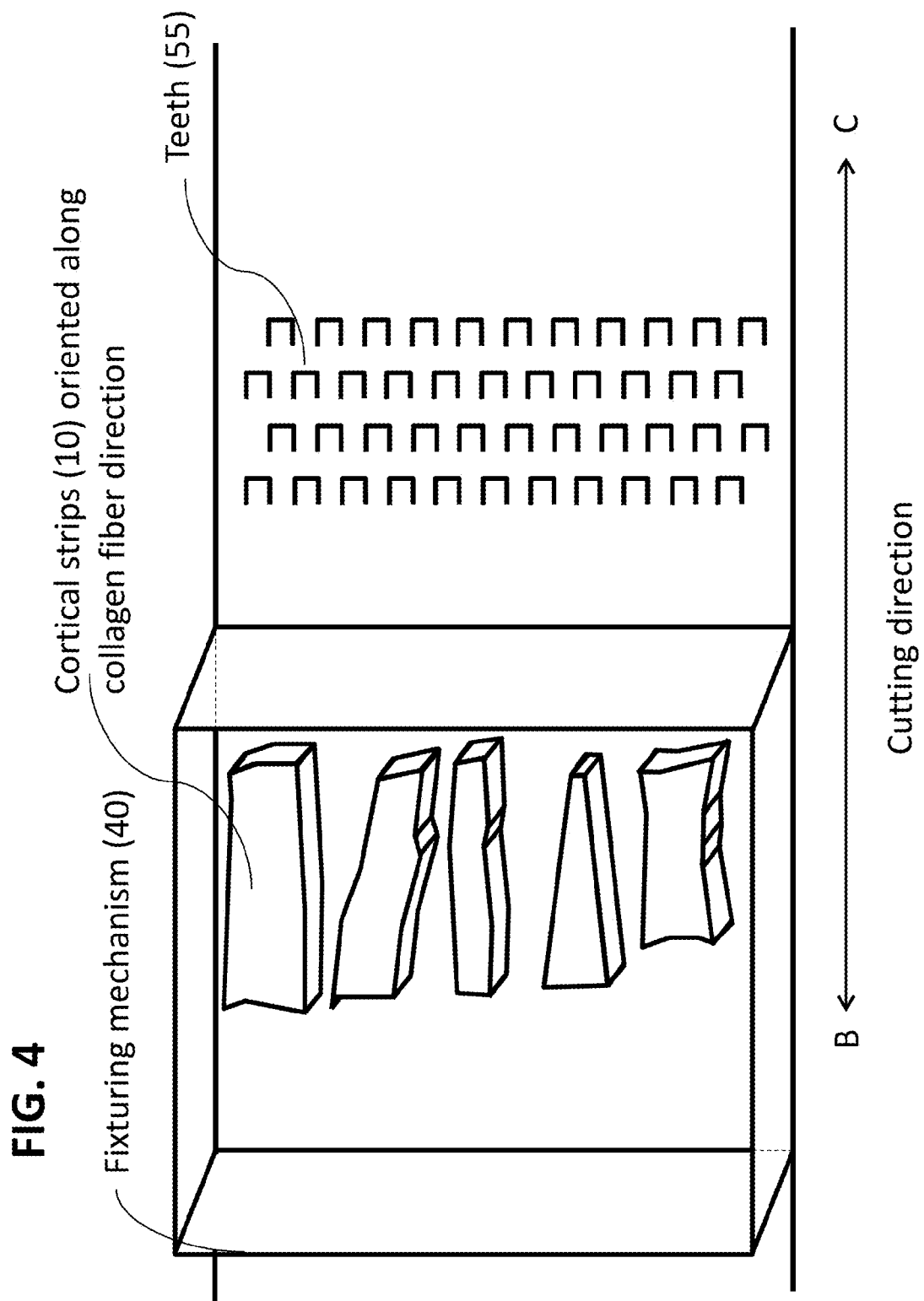

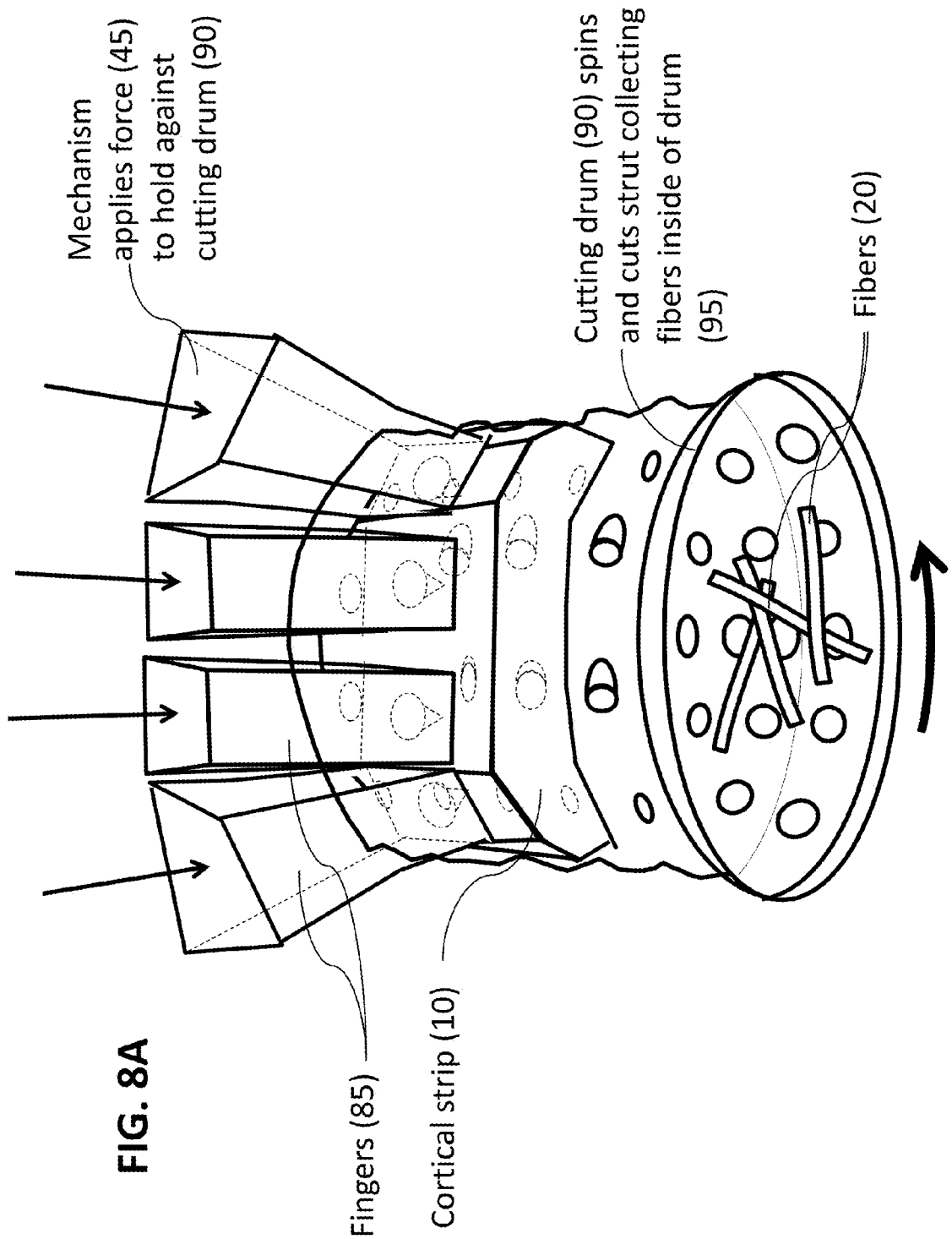

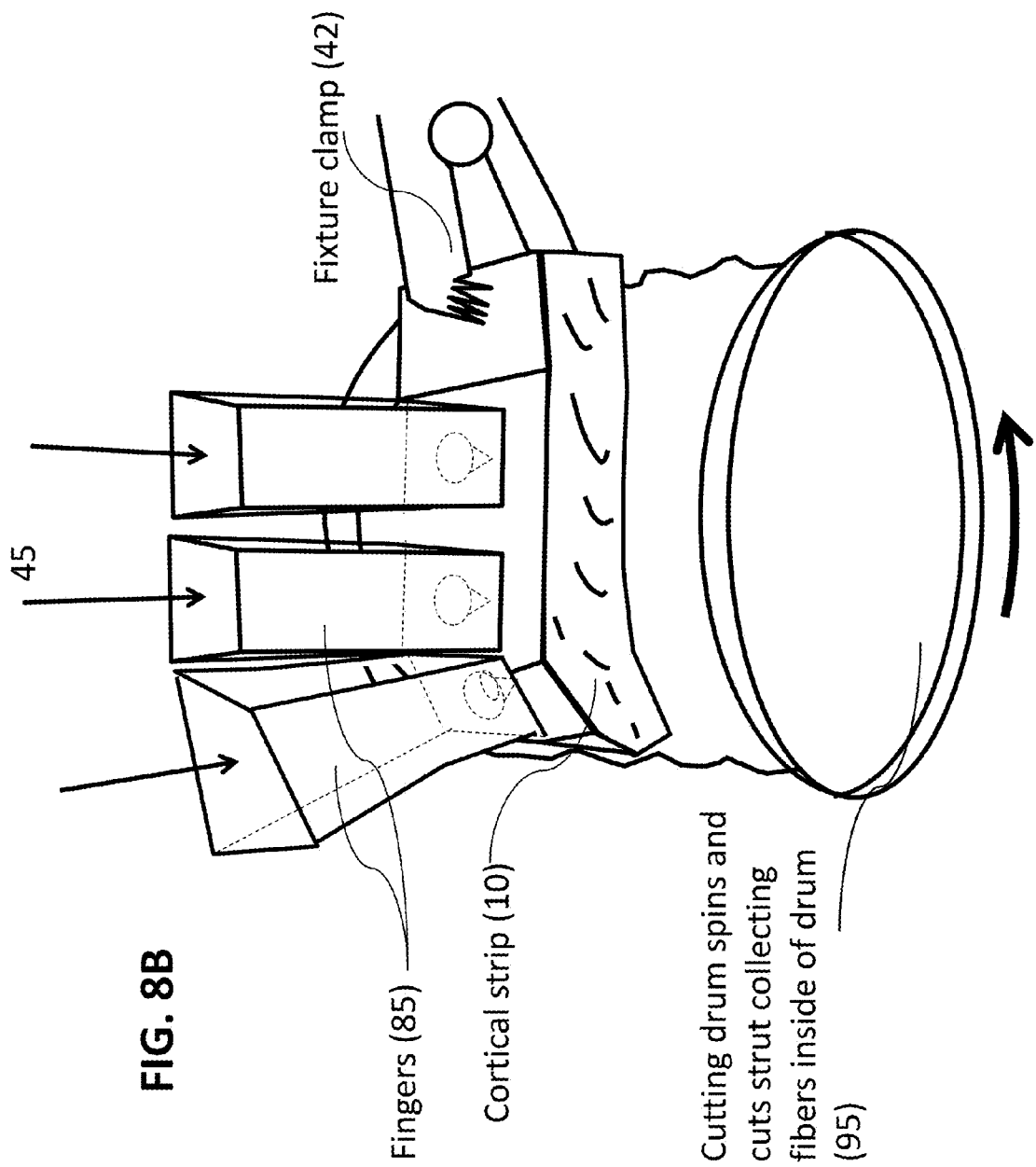

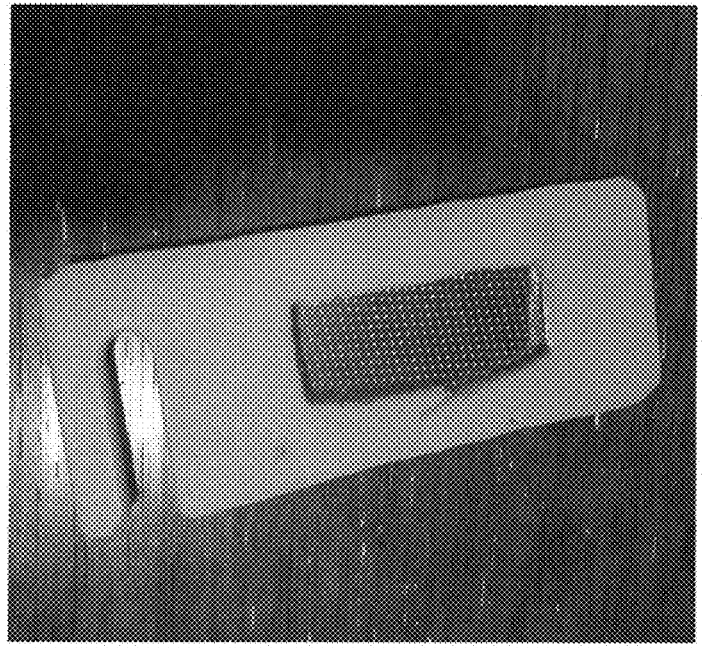
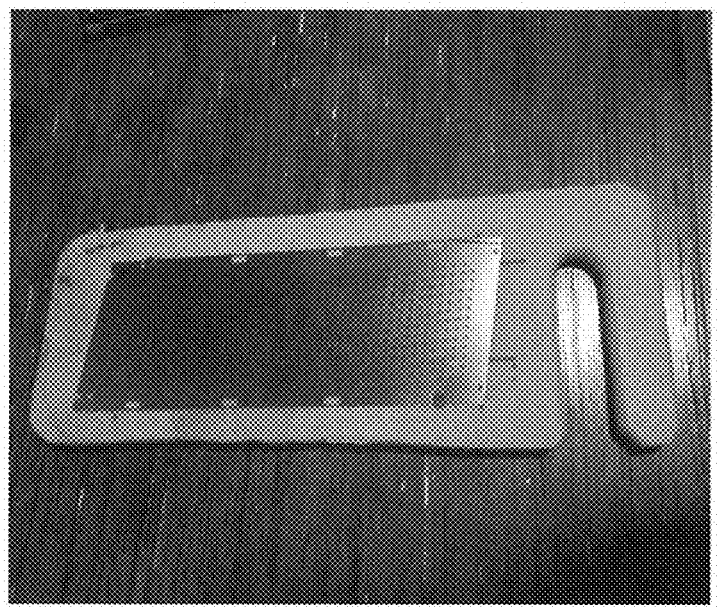

DEMINERALIZED BONE FIBERS HAVING CONTROLLED GEOMETRY AND SHAPES AND METHODS THEREOF

CROSS-REFERENCE TO RELATED APPLICATION(S)

This application is a continuation of U.S. patent application Ser. No. 14/256,911, filed Apr. 18, 2014, which is related to U.S. Provisional Application No. 61/814,192, titled "Material For Treating Bone Defects and Method For Making Bone Particles with Controlled Geometry," filed Apr. 19, 2013; U.S. Provisional Application No. 61/864,499, titled "Compositions of and Methods for Bone Particles Having Controlled Geometry," filed Aug. 9, 2013; and U.S. Provisional Application No. 61/952,128, titled, "Demineralized Bone Fibers Having Controlled Geometry and Shapes," filed Mar. 12, 2014, the entire contents of all of which are herein incorporated by reference.

BACKGROUND

Bone grafts are commonly used to treat defects in the skeletal system caused by injury or disease. Skeletal defects often require bone grafts to maintain space and provide a matrix for healing. A graft should provide or facilitate the various mechanisms of bone healing including osteoconduction, osteoinduction, and osteogenesis. Osteoconduction is the ability of the graft to act as a matrix or scaffold to support bone formation. Osteoinduction is a result of bone growth factors that stimulate differentiation of local cells to become bone forming cells, i.e. osteoblasts. Bone morphogenic proteins (BMP's) that are naturally occurring in bone, or that may be produced by recombinant gene technologies, are responsible for osteoinduction. Osteogenesis refers to the formation of bone, and may also be used to reference the ability of cells, to form bone. Bone forming cells may either be resident at the graft site or transplanted to the site by autogenous bone, bone marrow aspirate and/or cell implantation. Considering these requirements to form bone, a need exists for a reproducible and cost-effective process of making a bone graft having improved osteoconductive and osteoinductive properties.

SUMMARY

In some embodiments of the present invention, a bone repair composition includes a plurality of elongated bone fibers cut from demineralized bone. In some embodiments, the plurality of elongated bone fibers are in a form selected from a cavity, ball, pellet, sheet, strip, cylinder, cone, putty, gel, or injectable slurry.

In some embodiments of the present invention, the bone repair composition also includes autologous bone chips, bone marrow aspirate, a morcellized autograft, bone marrow cells, mesenchymal stem cells, oxygenating materials, oxygen generating compounds, growth factors, antibiotics, antineoplastic agents, or combinations thereof.

In some embodiments of the present invention, a method of producing an elongated bone fiber with controlled geometry from cortical bone includes demineralizing the cortical bone to form demineralized bone; and cutting the demineralized bone to form the elongated bone fiber.

In some embodiments of the present invention, the method above also includes forming at least one cortical bone strut from the demineralized bone, aligning the at least one cortical bone strut in an aqueous solution, and freezing the at least one cortical bone strut in the aqueous solution to form an ice block.

In some embodiments of the present invention, the method of producing an elongated bone fiber with controlled geometry from cortical bone includes repeatedly cutting the demineralized bone to form a plurality of elongated bone fibers. In some embodiments, the plurality of elongated bone fibers are at least 60% uniform.

In some embodiments of the present invention, a method of producing a sheet of elongated bone fibers with controlled geometry from bone includes demineralizing the bone to form demineralized bone, repeatedly cutting the demineralized bone to form a plurality of elongated bone fibers, and adding the plurality of elongated bone fibers to a mold to form a sheet of elongated bone fibers.

BRIEF DESCRIPTION OF THE DRAWINGS

The patent or application file contains at least one drawing executed in color. Copies of this patent or patent application publication with color drawings will be provided by the Office upon request and payment of the necessary fee.

These and other features and advantages of the present invention will be better understood by reference to the following detailed description when considered in conjunction with the accompanying drawings.

FIG. 4 is a schematic representation of a cutting device in which cortical strips are placed on a moveable fixturing means which moves across a cutting surface having a plurality of teeth, according to embodiments of the present invention.

FIG. 8A is a schematic representation of a drum grater cutting device showing a fixture clamp that holds an end of the bone material (e.g., cortical strip), according to embodiments of the present invention.

FIG. 8B is a schematic representation of the drum grater cutting device of FIG. 8A showing a mechanism that applies force to hold the bone material against the cutting surface inside the drum; and an inside cavity of the drum which collects cut bone fibers.

FIGS. 16A and 16B are photographs of a cutting blade incorporated into a plastic frame, according to embodiments of the present invention.

DETAILED DESCRIPTION

Figure 1:
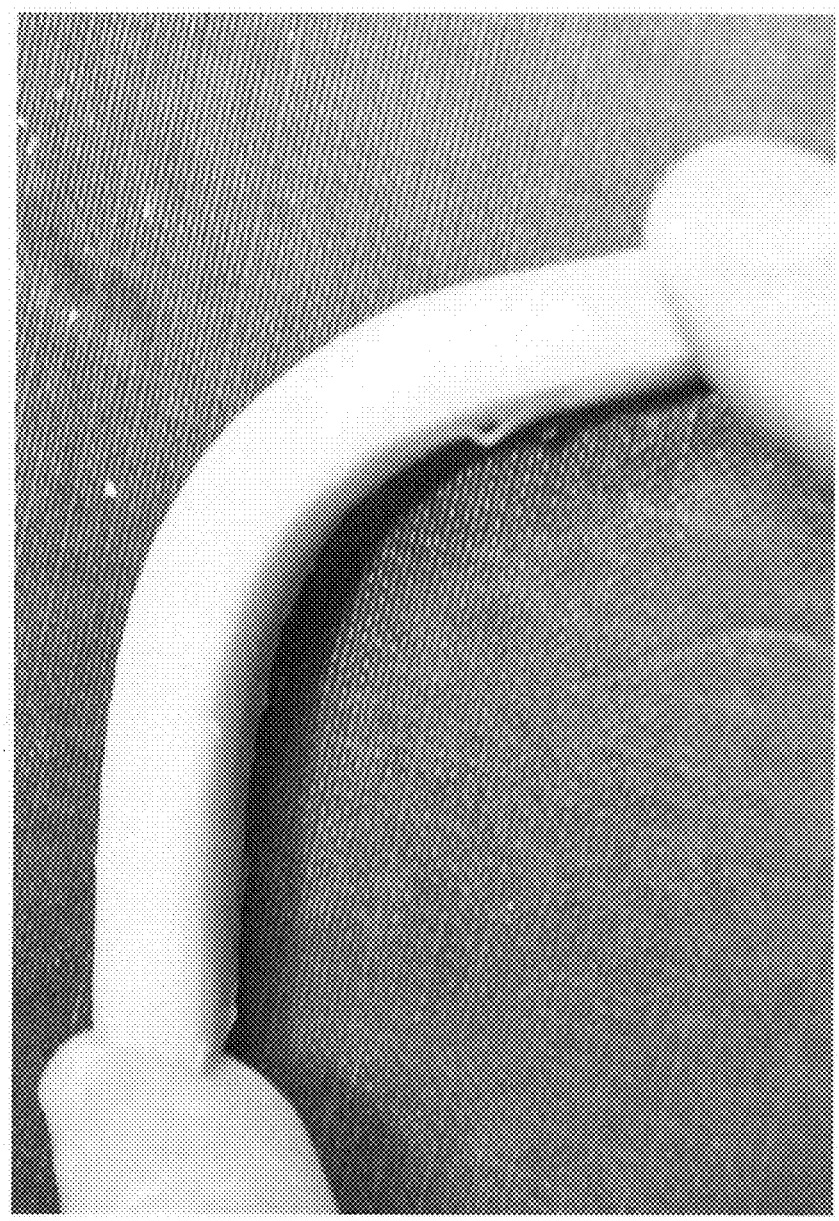
FIG. 1 is a photograph showing the flexibility of demineralized cortical strips prior to cutting, according to embodiments of the present invention.

Embodiments of the present invention describe methods for making bone fibers which may be used in bone grafts for treating bone defects. In some embodiments, the methods for making the bone fibers include demineralizing whole bone and subsequently cutting the demineralized bone in a direction parallel to the orientation of collagen fibers within the demineralized bone to form elongated bone fibers. The bone material of the present invention is derived from human (allograft) or animal (xenograft) cortical bone and is processed in such a manner to provide grafts of high utility based on the controlled geometry of the bone fibers. The methods of preparation of the graft provide improved efficiency and uniformity with reproducible results and decreased requirements for equipment and resulting costs. The bone graft forms of the present invention do not require the addition of exogenous materials to maintain the form of the graft. These improved characteristics will become apparent to one skilled in the art based upon the present disclosure.

As used herein, the term "cutting" refers to the process of using a blade or blades to mechanically cut, slice, shave, or saw material.

As used herein, the terms "fixturing" and "fixtured" refer to holding a material in a manner to allow for stabilization of the material in a cutting mechanism.

As used herein the terms "demineralized" and "demineralizing" refer to the demineralization of bone. That is, the decrease in the amount of calcium in the bone determines the amount of demineralization. As such, completely demineralized bone has no calcium, or only trace amounts of calcium. In some embodiments, completely demineralized bone has no more than 10% calcium.

As used herein, "medium grater" refers to a grater having teeth which are about 1.1 to about 4 mm wide and about 1.1 to about 4 mm thick.

As used herein, "fine grater" refers to a grater having teeth which are about 0.05 mm to about 1.0 mm wide and about 0.05 to about 1.0 mm thick.

As used herein, "approximately uniform" refers to at least 60% of a batch of cut elongated fibers made following the same process, using the same cutting mechanism, have approximately the same cross-sectional dimensions. That is, the "same" dimension refers to the same measurement within one standard deviation. In some embodiments the approximately uniform refers to at least 60% of a batch of cut elongated bone fibers having approximately the same length dimensions. In some embodiments, the approximately uniform bone fibers have the same cross-sectional and the same length dimensions.

As used herein, "fibers," "bone fibers," "elongated fibers," "elongated bone fibers," and "elongated bone particles" are used interchangeably to refer to fibers cut from cortical bone strips.

As used herein, "cortical bone strips," "cortical strips," "bone strips, "cortical bone struts," and "cortical struts," are used interchangeably to refer to strips of bone cut from whole cortical bone.

The bone fibers of the present disclosure are formed from whole bones which have been demineralized prior to cutting. In the present disclosure, whole bones or segments thereof are demineralized by first cleaning the bones and then treating the bones using a dilute acid solution to remove the mineral components (i.e., calcium), resulting in a material that is soft and malleable enough to allow it to be cut with precision blades. Suitable dilute acid solutions for demineralization include inorganic acids such as hydrochloric acid (HCl) or organic acids such as acetic acid (AcOH). Concentrations may range from about 0.3 N to about 3 N. Alternatively, chelating agents such as EDTA may be used for demineralization. Demineralization of bone requires diffusion of acid into the matrix of the bone. Stirring, sonicating and other mechanical means increase the rate of demineralization, and acid concentration should not exceed about 3N for HCl in order to preserve collagen integrity and osteoinductivity. Temperature may be regulated during demineralization and should not exceed about 40° C.

In some embodiments, the demineralized bone is fixtured in such a fashion as to allow for creating controlled geometry bone particles or fibers by using cutting tools with cutting dimensions which are designed to provide resulting fibers of preferred dimensions. The design and type of cutting tool is selected according to the desired geometry of the elongated fiber particle. According to aspects of embodiments of the present invention, the selected cutting tool, and in particular the mechanisms of the selected cutting tool are such that the plurality of elongated fibers formed from a demineralized bone strip are in the least mostly uniform such that the osteogenic properties of each fiber particle is approximately the same. As such, the way in which a fiber is formed effects the dimensions and surface area of the fiber, and when the fibers are formed into various 3-dimensional forms (e.g., strips) their shape influences the porosity and other properties of the structure. The number of pores (i.e., density) and the size of pores affect the inherent osteogenic properties of the implant. In this way, fibers having approximately uniform structures are formed, and these approximately uniform fibers may be combined to form various implant shapes having more consistent and approximately homogenous characteristics throughout. Some of the properties of each fiber include fiber size (i.e., length, width and thickness), surface area, and the ability to swell with rehydration, cohesiveness, and compression resistance. The ability to control the geometry of the elongated fiber particles of the present invention allows for more uniform and reproducible bone implants made from these elongated fiber particles.

An aspect of embodiments of the present invention is the capability to cut the bone while it is fully hydrated. Cutting a hydrated bone facilitates the cutting process by making it softer and more lubricious as well as avoiding steps to prepare the bone for cutting, e.g. drying to avoid it sticking to moving blades as occurs during milling. The potential for the bone to go from demineralization to cutting and final product formation in a seamless manner offers significant efficiency opportunities for the overall process. The ability to reduce handling steps also avoids the potential for degradation of the osteogenic properties of the demineralized bone fiber.

Another aspect of embodiments of the present invention is the ability to control the cutting direction along the long axis of the bone. As such, the demineralized bone is cut in the direction of the collagen fibers to form elongated fiber particles. By cutting in this direction the resulting long, thin elongated fiber particles maintain strength as compared to fibers that are cut across the fiber alignment. Cutting along the collagen fiber direction also allows for more precise cutting.

In some embodiments of the present invention, the malleability of the demineralized bone allows the bone to be fixtured such that it can be held flat or stable for cutting. By presenting a flat surface to the cutting tool, the precision of the cutting process is greatly enhanced. This allows for control of the process and limits waste, making it a process that is efficient from a yield perspective, which is particularly important for allograft tissue due to the scarcity and cost of donated tissue. Furthermore, control of the dimensions of the resulting material allows for the ability to engineer the final product for optimal handling and performance characteristics.

The fibers may vary in their dimensions such as length, width and thickness according to the intended applications. The ability to control these parameters with precision allows for the possibility of tissue-engineered constructs. The use of the controlled geometry particles to make a range of forms is contemplated in the present invention.

The process according to embodiments of the present invention forms an elongated fiber particle having a length from about 1 cm to about 30 cm. In some embodiments, an elongated fiber particle of the present invention has a length from about 3 cm to about 18 cm. In other embodiments, an elongated fiber particle of the present invention has a length from about 3 cm to about 10 cm. In still other embodiments, an elongated fiber particle of the present invention has a length from about 4 cm to about 8 cm.

The process according to embodiments of the present invention forms an elongated fiber particle having a width from about 0.05 mm to about 4 mm. In some embodiments, an elongated fiber particle of the present invention has a width from about 0.2 mm to about 1 mm. In other embodiments, an elongated fiber particle of the present invention has a width from about 0.5 mm to about 1 mm.

The process according to embodiments of the present invention forms an elongated fiber particle having a thickness from about 0.05 mm to about 4 mm. In some embodiments, an elongated fiber particle of the present invention has a thickness from about 0.2 mm to about 1 mm. In other embodiments, an elongated fiber particle of the present invention has a thickness from about 0.5 mm to about 1 mm.

The cutting technique also allows for equipment that is more precisely oriented than the techniques in the art that require heavy grinding or milling. The design constraints for allograft bone processing include: small batch (e.g., bone from 1 donor), sterile process environment that is easy to clean and sterilize, high cost/value raw material, and the need to preserve the osteogenic properties (e.g., collagen structure and bone morphogenic proteins (BMPs)). All of these design constraints for allograft bone processing require custom made equipment for execution of this specialized purpose.

Embodiments of the present invention provide: the ability to control the geometry of resulting fiber dimensions, improved efficiency and ease of fiber production, and a high yield with low waste process of making elongated fibers from demineralized bone. It was reported that the configuration of the fibers also influences the biological response to them as disclosed in Martin G. J. et al, Spine 24(7):637-645, 1999, the entire contents of which are herein incorporated by reference. Accordingly, the ability to control the geometry of demineralized bone particles offers the opportunity to control the physical dimensions of the fibers, and construct designs that improve the biological response with the aim to maximize the bone healing response.

Methods for Forming Elongated Fiber Particles

Elongated fiber particles of the present invention are derived from any whole bone. The whole bone is cleaned of extraneous tissue and cut to remove metaphyses, thereby providing cortical shafts of the humerus, femur, tibia, fibula, etc. Shafts are cut to length and split lengthwise into cortical strips as appropriate for the final geometry of the desired bone fiber product form.

Demineralization.

In order to demineralize the cortical struts effectively and efficiently, the thickness of the strut, the concentration of acid and length of time in acid are all variables to consider. The demineralization reaction occurs as the acid penetrates into the bone, such that it occurs along a diffusion front. Cortical struts cut to <8 mm thick allow for more efficient demineralization as the greatest diffusion distance is 4 mm.

In some embodiments, cortical strips are demineralized using dilute acid (e.g., 0.3-0.6 N hydrochloric acid) by soaking in a stirred bath at room temperature or controlled temperature. In some embodiments, 20 ml 0.6 N HCl is used per 1 gram of bone for 1-7 days. The dilute acid is replaced periodically (e.g., at least every 24 hours) with fresh dilute acid, and soaking is continued until the bone is bendable by hand, as shown in FIG. 1. In some embodiments, cortical strips are demineralized in at least 0.3N acid and up to, but not more than, 3N acid. The ability to flex the bone easily to 180 degrees is an indication of full demineralization. Demineralization is optimized and adapted depending on the type of bone. One of ordinary skill in the art readily recognizes that human bone is more porous than some animal bones (e.g., bovine and porcine bones) which have a plexiform architecture that may be more difficult to penetrate and demineralize. Demineralization may be readily optimized (e.g., duration of acid soak, temperature, and/or concentration of acid) according to the type of bone selected.

Cutting Devices.

The demineralized cortical bone strips are subsequently fixtured into a cutting device such that the long axis of the cortical strip, which correlates to the direction of collagen fibers, is parallel to the cutting direction such that the collagen fibers are cut along their length.

The dimensions of the cortical strip control the overall size and geometry. The selected cutting tool controls the particle size, and is selected depending on the requirements for the final product form. For example, elongated fiber particles having long aspect ratios, cortical strips (5 cm long and 1-5 cm wide of varying thickness depending on anatomy) are demineralized. A cutter that forms fibers 0.1 mm thick by 2 mm wide may be used. Cutting devices that are capable of forming various fiber dimensions are disclosed herein. That is, in addition to demineralizing the bone prior to cutting, the cutting mechanisms of the selected cutting device also contribute to the ability to form approximately uniform fiber particles with high yields.

Figure 2A:
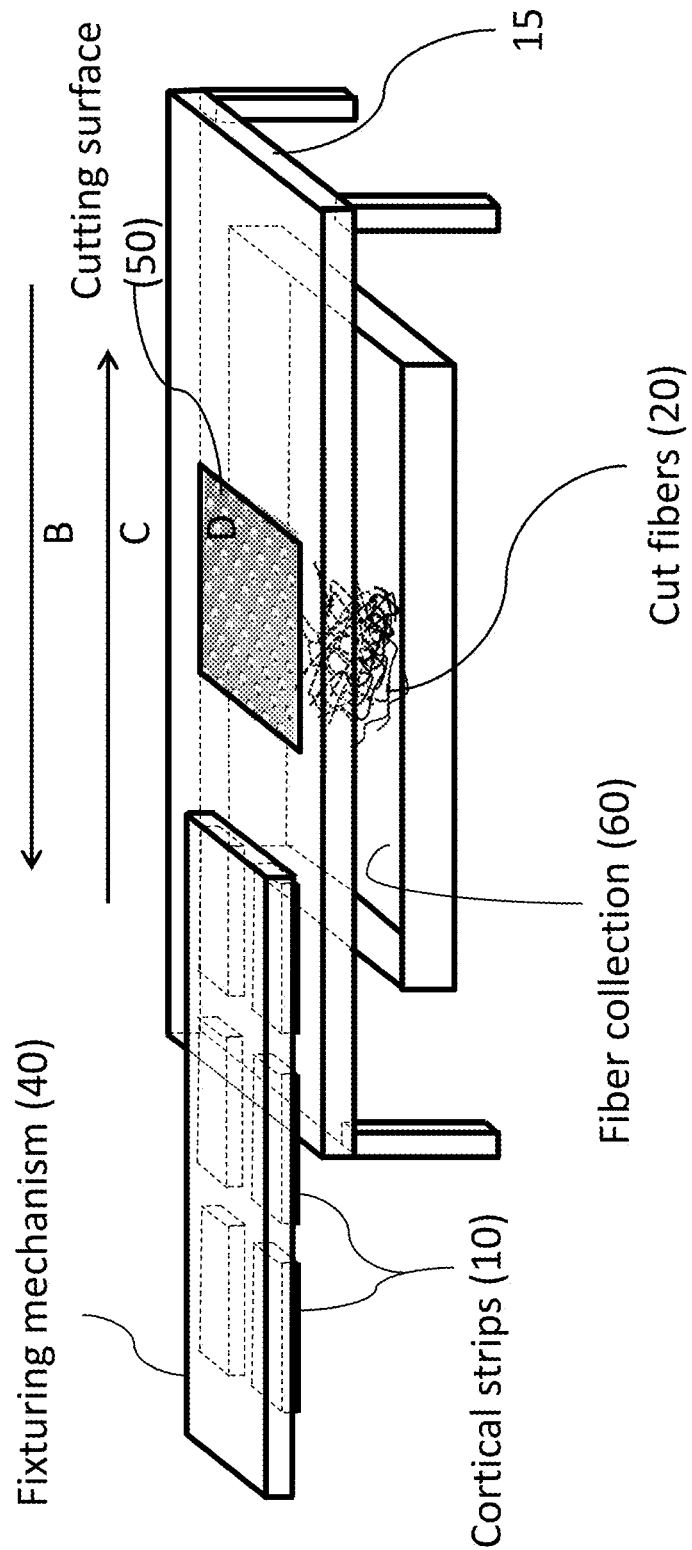
FIG. 2A is schematic representation of a cutting device in which demineralized cortical strips (10) are fixtured to a fixturing mechanism (40) thereby allow for the cortical strip to be moved in direction B and C with left and right sliding movement such that the cortical strip passes over the cutting surfaces of cutting element (50), according to embodiments of the present invention.
Figure 2B:
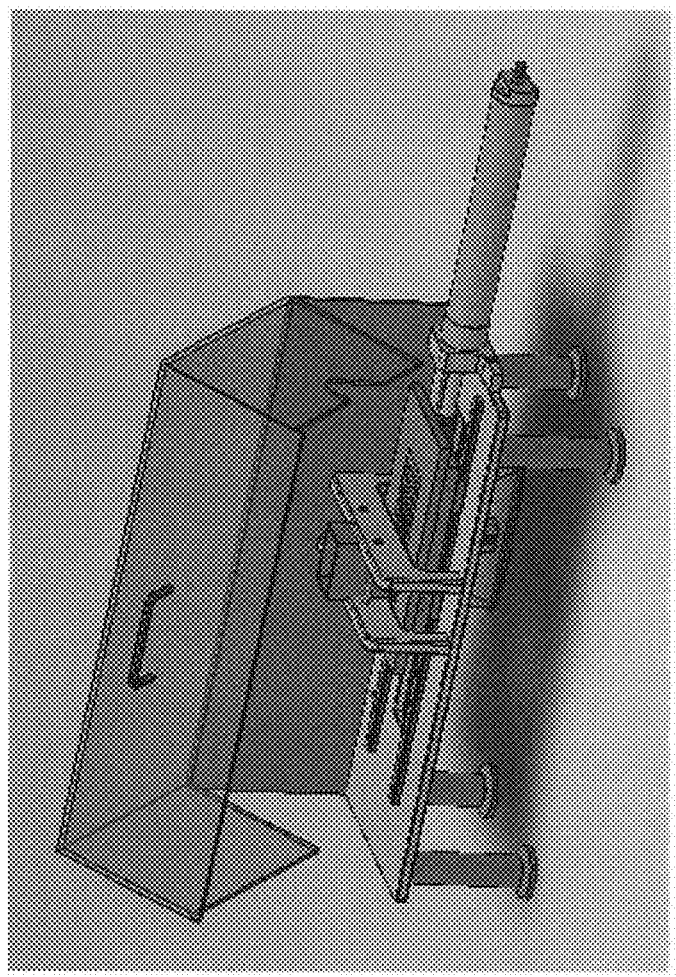
FIG. 2B is an alternative representation of a cutting device having the same features as described in FIG. 2A.

Non-limiting examples of cutting devices and mechanisms are disclosed herein. With reference now to the embodiment illustrated in FIGS. 2A, 2B, a cutting assembly used to form elongated bone particles from demineralized cortical strips (10) is schematically depicted. In FIG. 2A, the illustrated embodiment, the cutting assembly includes a fixturing mechanism (40) configured to support the demineralized cortical strips, a support member (e.g., a table or work bench) configured to support a cutting element (50), and a fiber collection member (60) positioned below the support member to collect the cut elongated bone fibers (20). The cutting element D includes a plurality of teeth (55) configured to cut the demineralized cortical strips (10) into the cut elongated bone fibers (20). In the illustrated embodiment, the fixturing mechanism includes an upper surface and a lower surface opposite the upper surface. The cortical strips are attached to the lower surface of the fixturing mechanism (40) and the cutting element is attached to an upper surface of the support member. Accordingly, the cortical strips are disposed between the lower surface of the fixturing mechanism and the upper surface of the support member on which the cutting element is attached. The fixturing mechanism (40) is configured to slide in a reciprocating manner (arrows B and C) along the support member such that the teeth (55) on the cutting element (50) may engage the demineralized cortical strips to form the bone fibers (i.e., the cortical strips affixed to the slidable fixturing mechanism are configured to be passed back and forth over the teeth (55) on the cutting element (50) to form the elongated bone fibers (20).

Figure 3A:
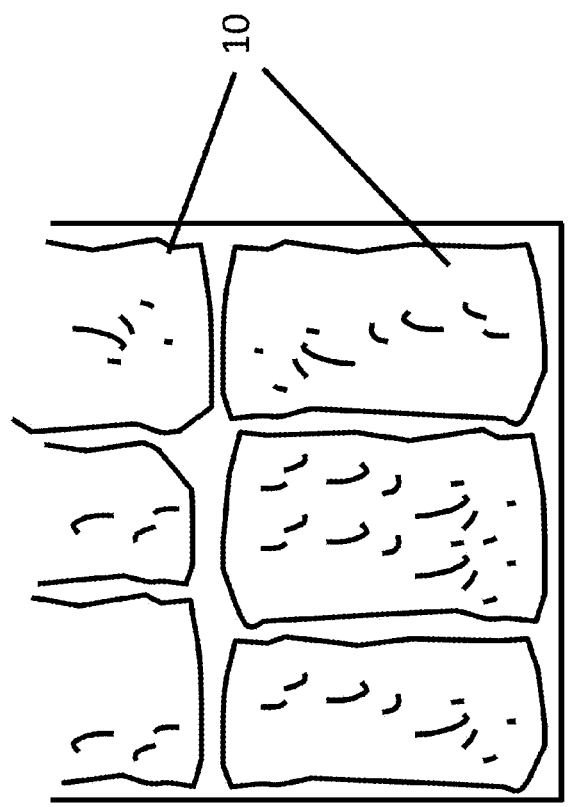
FIG. 3A is a schematic representation of a fixturing structure that holds demineralized bone material (e.g. cortical strips) to allow for uniform downward pressure on the cortical strips being cut when the fixturing structure moves across the cutting surface; the demineralized cortical strips are oriented so that the fibers are cut lengthwise (e.g. proximal to distal) in the direction of collagen fibers within the bone, according to embodiments of the present invention.

With reference now to FIG. 3A, the demineralized cortical strips (10) attached to the lower surface of the fixturing mechanism are depicted. In the illustrated embodiment, the demineralized cortical strips are oriented lengthwise (e.g. proximal to distal) along the fixturing mechanism such that collagen fibers within the cortical strips are oriented substantially parallel to the directions (arrows B and C) in which the fixturing mechanism is configured to slide in a reciprocating manner across the cutting element D (i.e., the cortical strips are attached to the fixturing mechanism such that the collagen fibers within the cortical strips are aligned parallel with the cutting directions). Accordingly, in illustrated embodiment, the cutting assembly is configured to cut the collagen fibers of the cortical strips lengthwise.

Figure 3B:
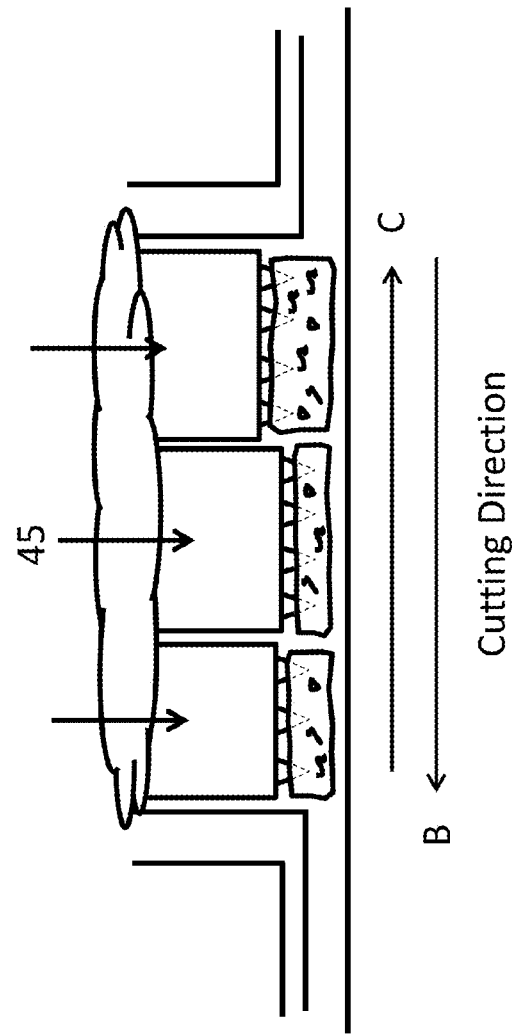
FIG. 3B is a schematic representation depicting lateral movement of the fixturing means of FIG. 2A across the cutting surface of a cutting device, according to embodiments of the present invention.

Additionally, as described in more detail below, the fixturing mechanism is configured to enable uniform downward pressure (45) to be applied to the demineralized cortical strips (10) as the cortical strips are passed back and forth across the cutting element to form the cut bone fibers. The application of uniform downward pressure (45) facilitates the production of approximately uniform elongated bone fibers. FIG. 3B depicts the application of uniform downward pressure on the non-uniform cortical strips which are then cut by the teeth of the cutting member in the indicated cutting directions (see arrows B and C in FIG. 2A).

With reference now to FIG. 4, a plurality of non-uniform demineralized cortical bone strips (10) are illustrated attached to the lower surface of the fixturing mechanism (40). As described above the fixturing mechanism is configured to slide in a reciprocating manner across the teeth (55) of the cutting element (50). As the teeth (55) of the cutting element engage the demineralized cortical bone strips, the teeth dig into the surface of the demineralized cortical bone strips and form elongated bone fibers. In the illustrated embodiment, the cutting member includes four rows of teeth, although the cutting member may have any other suitable number of rows of teeth, such as, for example, one to ten rows of teeth. Additionally, each of the teeth in the first row (i.e., the row of teeth configured to make initial contact with the demineralized cortical bone strips as the fixturing mechanism is slid in direction C toward the cutting element 50, as illustrated in FIG. 2) are spaced apart by a gap from adjacent teeth in the first row. The teeth in the second row of teeth (i.e., the row of teeth to the right of the first row of teeth in FIG. 4) are offset or staggered relative to the teeth in the first row of teeth. In the illustrated embodiment, the teeth in the second row of teeth are aligned with the gaps between the teeth in the first row. Together, the teeth in the first and second rows of teeth are configured to engage and cut the entire surface of the demineralized cortical bone strips (i.e., together, the first and second rows of teeth define a continuous cutting element). Otherwise, portions of the demineralized cortical bone strips corresponding to the positions of the gaps between the teeth would not be cut as the fixturing mechanism is slid back and forth across the cutting element. In the illustrated embodiment, the third and fourth rows of teeth are positioned the same or similar to the teeth in the first and second rows of teeth, although the teeth in the third and fourth rows may be positioned differently than the teeth in the first and second rows of teeth and still fall within the scope and spirit of the present disclosure. Additionally, in the illustrated embodiment, the teeth on the cutting member are rectangular, although the teeth may have any other suitable shape, such as semi-circular or triangular, and still fall within the scope and spirit of the present disclosure.

Figure 5A:
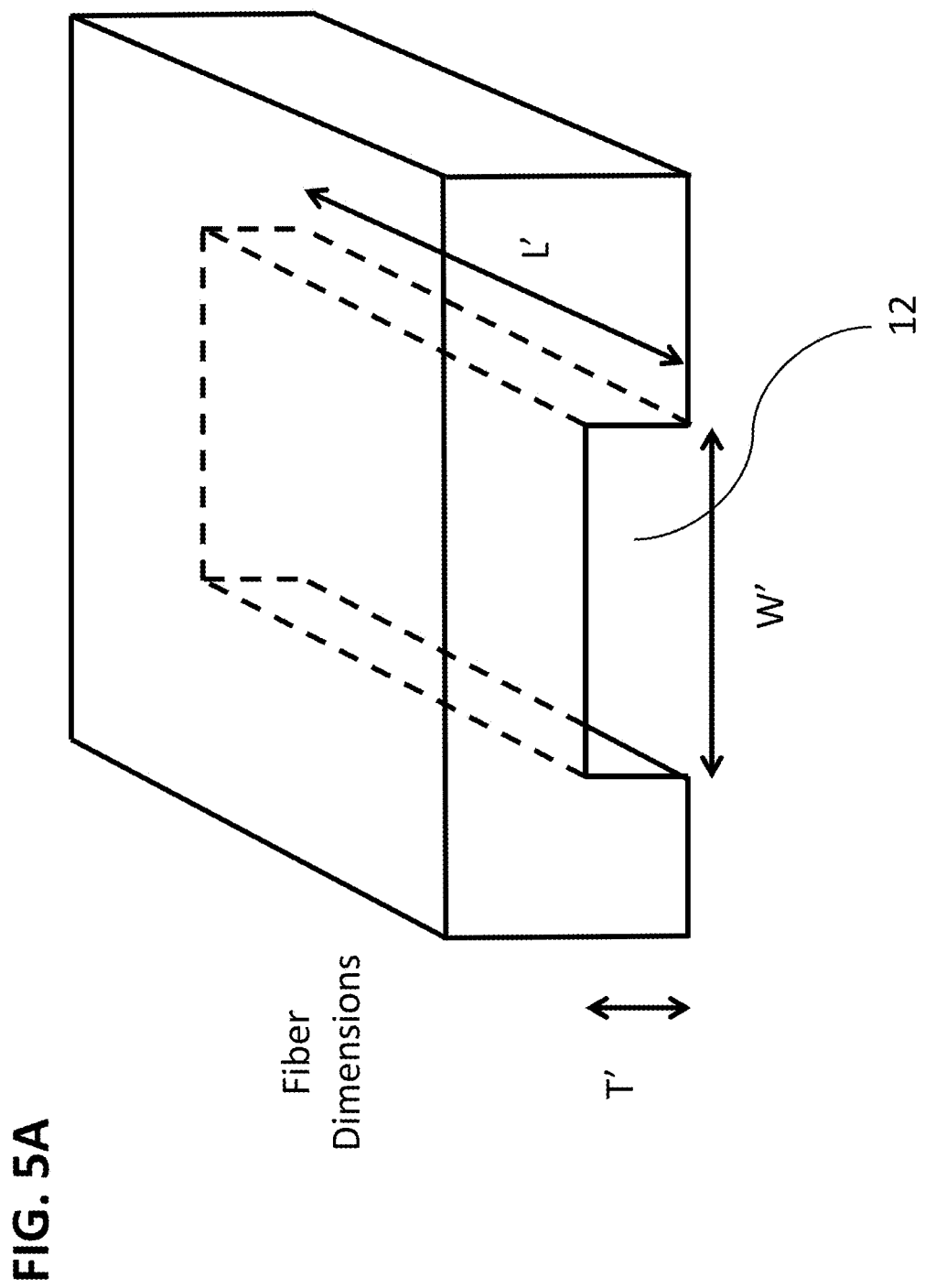
FIG. 5A is a schematic representation showing dimensions of an elongated fiber particle having a thickness (T'), a width (W'), and a length (U), according to embodiments of the present invention.

FIG. 5A illustrates a groove or channel (12) formed in a demineralized cortical bone strip due the engagement between the cortical bone strip and the cutting element (i.e., FIG. 5A illustrates a groove cut into the cortical bone strip by a tooth on the cutting element). In the illustrated embodiment, the groove in the demineralized cortical bone strip is shaped as a right rectangular parallelepiped, although the groove may have any other shape depending upon the shape of the teeth in the cutting element. It will be appreciated that the size and shape of the grooves (12) formed in the cortical bone strip correspond to the size and shape of the elongated bone particles or fibers cut from the cortical bone strip (10). In the illustrated embodiment, the groove in the cortical bone strip, and the corresponding bone fiber cut from the cortical bone strip, has a thickness T', a width W', and a length L'.

Figure 5B:
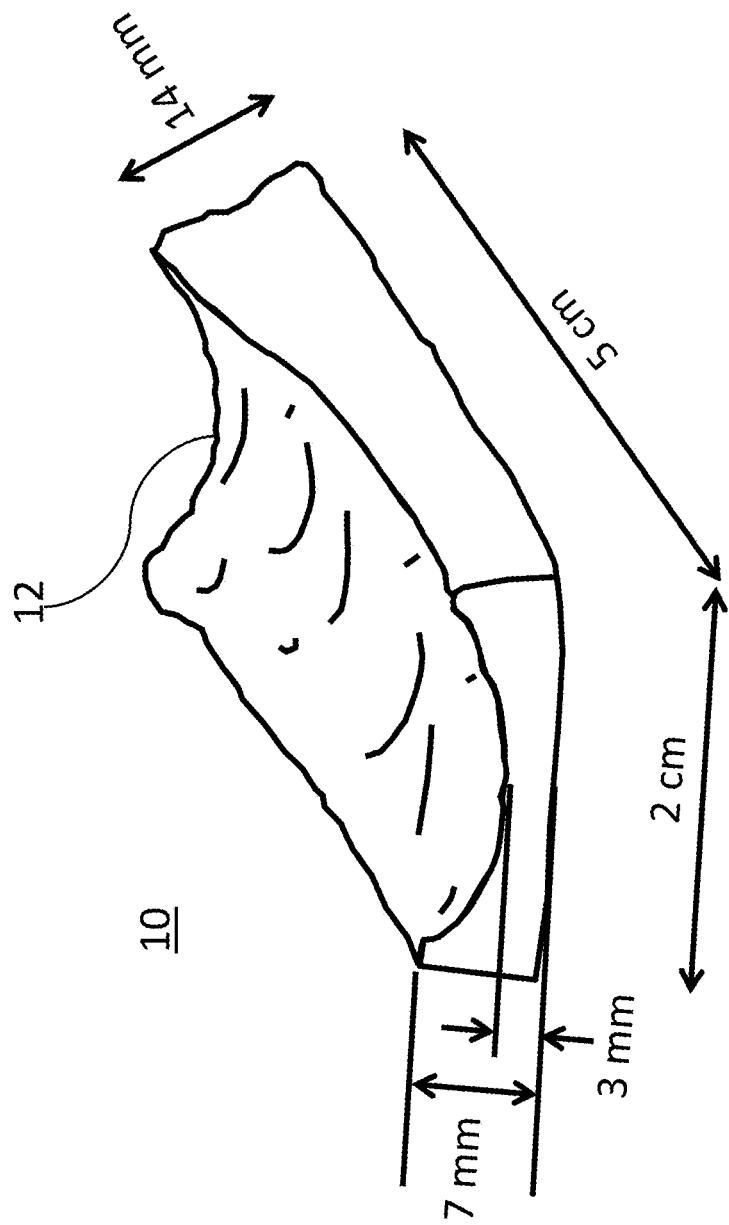
FIG. 5B is a schematic representation of an example cortical strip having non-uniform dimensions with a plurality of thicknesses throughout, some of which are indicated, and at least one width and one length, according to embodiments of the present invention.

Cortical bone strips cut from whole bone are not necessarily uniform. Instead, cortical bone strips may vary in width, length, and thickness. FIG. 5B depicts an exemplary embodiment of a non-uniform (i.e., asymmetrical) cortical bone strip having a groove (12). In the illustrated embodiment, one end of the cortical bone strip is approximately 14 mm thick and an opposite end of the cortical bone strip is approximately 7 mm thick, although the cortical bone strips may have other dimensions depending upon the source of the bone strips, such as, human (allograft) or animal (xenograft) cortical bone, and the type of bone, such as, femur, tibia, humerus, fibula, radius, or ulna.

In order for the cutting assembly of the present disclosure to produce approximately uniform bone particles or fibers from non-uniform bone strips, the fixturing mechanism may be configured to compensate for the variation among the various bone strips attached to the fixturing mechanism. In particular, the fixturing mechanism may be configured to compensate for variations in and among the cortical bones strips such that substantially flat, uniform surfaces of each of the cortical bone strips are presented to the teeth on the cutting element. In the embodiment illustrated in FIG. 6A, one of the non-uniform cortical bone strips is illustrated recessed in a channel in the fixturing mechanism and supported within the channel (75) by three floating support members (65). In one or more alternate embodiments, each cortical bone strip may be supported by any other suitable number of floating support members (65), such as, for instance, one to five floating support members. Other cortical bone strips may be supported on the fixturing mechanism in the same or similar manner as the cortical bone strip illustrated in FIG. 6A.

Figure 6A:
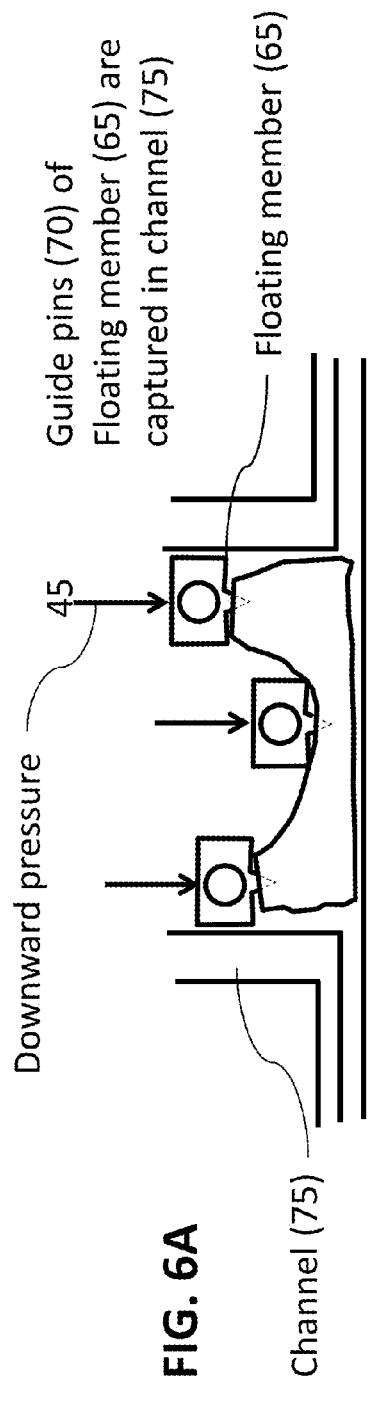
FIG. 6A is schematic representation of a side view of a fixturing means retaining bone material in place and contacting the bone material at some of its plurality of thicknesses, according to embodiments of the present invention.

With continued reference to FIG. 6A, each of the floating support members includes a rod or bar and a pair of guide pins (70) disposed on opposite ends of the rod which attach to the channel (75) attached to the fixturing mechanism (40). Each of the rods of the floating support members are attached to an upper surface of the cortical bone strip opposite the bottom surface of the bone strip which is configured to be engaged by the teeth on the cutting element. The rods of the floating support member may be attached to the cortical bone strips by any suitable means, such as, for instance, a series of ridges or spikes which pierce into the upper surfaces of the bone strips.

Figure 6B:
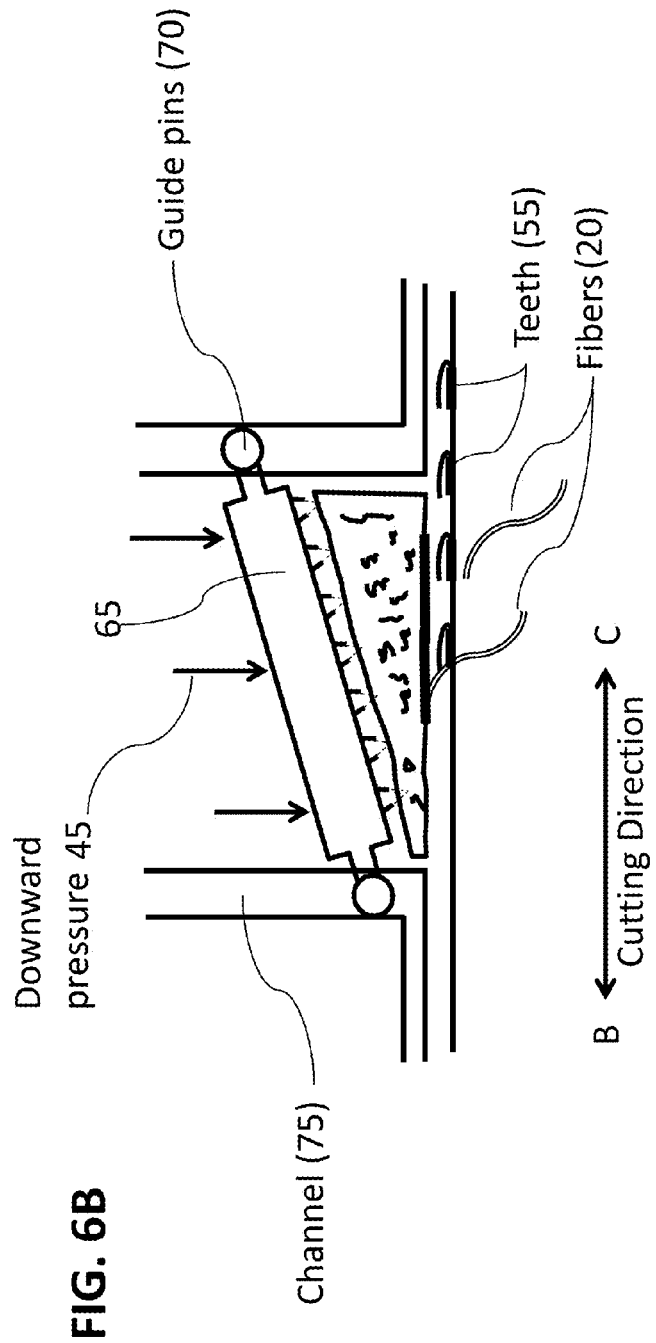
FIG. 6B is a schematic representation of an end view of a fixturing means retaining bone material (e.g., cortical strip) in the cutting device, according to embodiments of the present invention.

With reference now to the embodiment illustrated in FIG. 6B, the guide pins (70) on the floating support member (65) are slidably positionable along a pair of rails or channels (75) in the fixturing mechanism (40). The position and orientation of the floating support members, and thus the position and orientation of the cortical bone strips to which the floating support members are attached, may be set by sliding the guide pins up or down along the rails or channels in the fixturing mechanism. Accordingly, the position of the guide pins along the rails or channels can be adjusted to accommodate the unique sizes and shapes of non-uniform cortical bone strips such that a substantially flat bottom surface of each of the cortical bone strips protrudes out of the channels (i.e., the guide pins are configured to be adjusted depending upon the unique shape and size of the particular cortical bone strips supported by the floating support members such that generally uniform, flat bottom surfaces of each of the cortical bone strips are exposed). The substantially flat bottom surfaces of the cortical bone strips which protrude out of the channels are configured to be evenly cut by the teeth on the cutting element to produce substantially uniform elongated bone particles (i.e., the floating support members are configured to orient and position the cortical bone strips, including non-uniform cortical bone strips, such that the teeth on the cutting element evenly engage the cortical bone strips as the fixturing mechanism is slid in a reciprocating manner across the cutting element).

Additionally, the guide pins may be spring-loaded (or biased by any other resilient member) to provide a generally uniform downward pressure on the cortical bone strips which tends to cause a portion of the cortical bone strip to protrude from the channel. Accordingly, as bone particles or fibers are scraped away from the surface of the cortical bone strips by the teeth, the springs or other resilient members coupled to the guide pins tend to maintain a surface of the cortical bone protruding from the channel in the fixturing mechanism such that additional bone particles or fibers may be scraped off of the surface of the cortical bone strip. Additionally, the equal downward pressure supplied throughout the cortical bone strip by the spring-loaded guide pins allows for a flat surface of the cortical bone to be presented to the cutting element to ensure even contact of the cutting teeth against the cortical bone strips.

Figure 7:
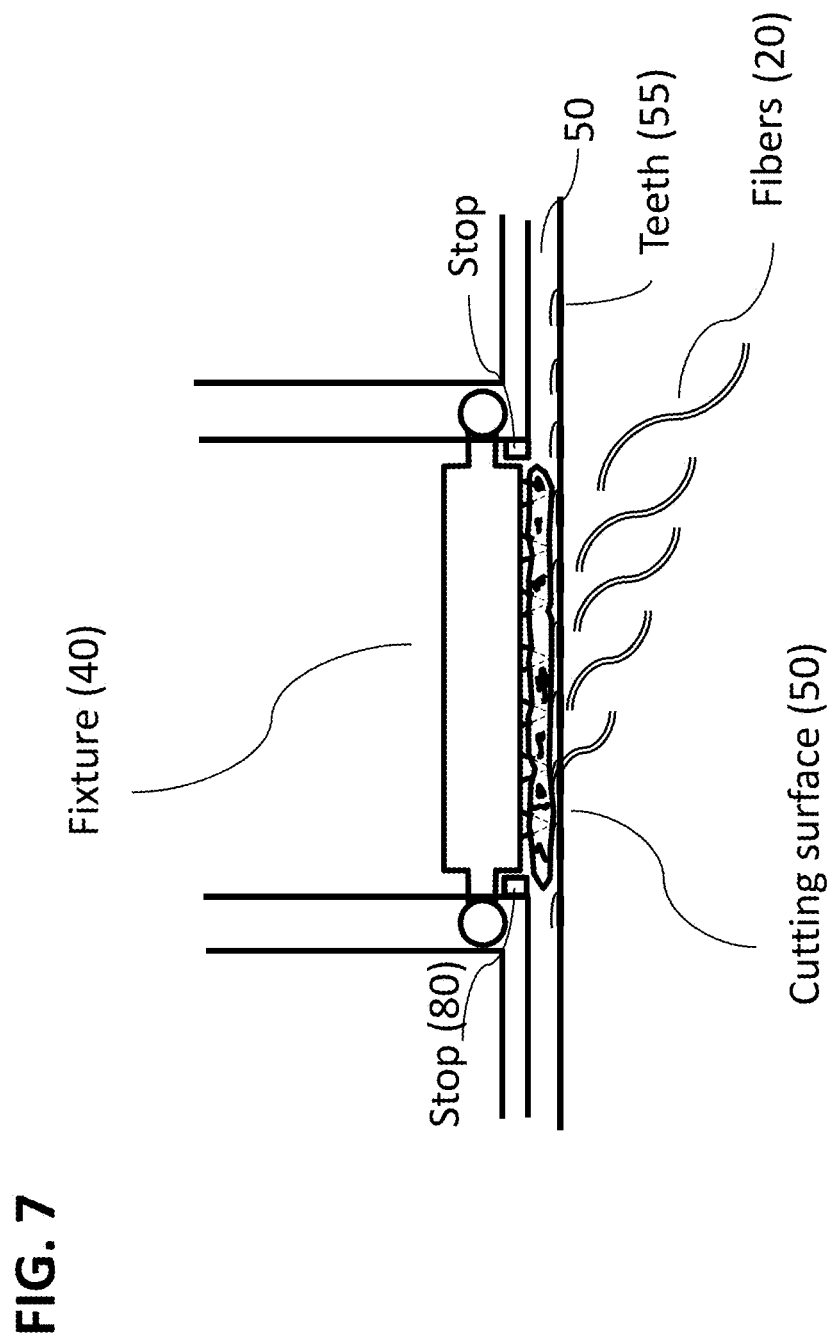
FIG. 7 is a schematic representation of a cutting device in which a fixturing means retaining bone material is on top of a cutting surface, according to embodiments of the present invention.

With reference now to the embodiment illustrated in FIG. 7, the fixturing mechanism includes a plurality of stops (80) configured to prevent the floating support members from contacting the teeth on the cutting element (i.e., the stops (80) are configured to prevent any portion of the floating support member (65) from protruding out of the channel (75) and engaging the teeth (55)). In the illustrated embodiment, the stops are located near the bottom of each of the rails or channels along which the guide pins are configured to slide. In the illustrated embodiment, the stops are configured to abut against the rods to prevent the floating support members (65) from protruding out of the channel and thereby contacting the teeth on the cutting element as the fixturing mechanism (40) is slid in a reciprocating manner across the cutting element (50).

With reference now to FIG. 8A, a cutting assembly according to another embodiment of the present disclosure is illustrated. In the illustrated embodiment, the cutting assembly includes a cylindrical drum-type grater configured to cut elongated fiber particles or fibers from cortical bone strips. An outer surface of the cylindrical drum (90) includes a plurality of teeth or blades configured to dig into the cortical bone strips to produce the elongated bone fibers. In the illustrated embodiment, the cortical bone strip is wrapped along the outer surface of the cylindrical drum. A fixturing mechanism applies a downward pressure (45) to hold the cortical bone strip against the outer surface of the drum to maintain contact and engagement between the teeth/blades and the cortical bone strip. As the cylindrical drum rotates, the teeth/blades on the outer surface of the drum engage a bottom surface of the cortical bone strip and thereby cut the elongated bone fibers from the cortical bone strip. In the illustrated embodiment, the elongated bone fibers are collected in a central cavity (95) defined by cylindrical drum. In one or more alternate embodiments, the elongated bone fibers may be collected in a separate chamber or compartment housed within the central cavity (95) of the cylindrical drum. The fixturing mechanism may include any suitable structure which is configured to maintain the cortical strip in contact with the teeth/blades on the cylindrical drum. For instance, as illustrated in the embodiment of FIG. 8A, the fixturing mechanism (40) may include four fingers (85) configured to apply a downward pressure (45) across an upper surface of the cortical strip to maintain contact between the bottom surface of the cortical strip and the teeth/blades on the cylindrical drum (90). As illustrated in the embodiment of FIG. 8B, the fixturing mechanism may include a fixture clamp (42) configured to maintain one end of the cortical strip (10) in contact with the teeth/blades on the cylindrical drum and three fingers (85) configured to apply a downward pressure across the remainder of the upper surface of the cortical strip. Although in the illustrated embodiments of FIGS. 8A and 8B the fixturing mechanism includes four fingers and three fingers, respectively, the fixturing mechanism may have any other suitable number of fingers, such as, for example, one to six fingers (85).

Figure 9:
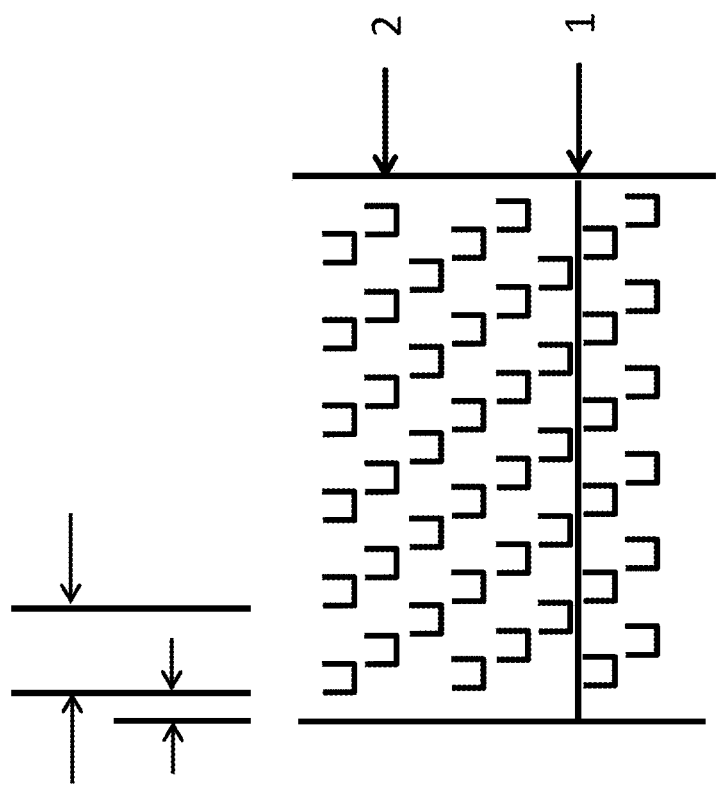
FIG. 9 is a schematic representation of a cutting surface having cutting teeth arranged as shown, according to embodiments of the present invention.

With reference now to the embodiment illustrated in FIG. 9, the teeth on the outer surface of the cylindrical drum may be arranged in a series of eight rows. In the illustrated embodiment, each of the teeth in the first row (i.e., the bottom row of teeth in FIG. 8 that is configured to make initial contact with the demineralized cortical bone strips as the cylindrical drum rotates, as illustrated in FIGS. 8A and 8B) are spaced apart by a gap from adjacent teeth in the first row. The teeth in the second and third rows of teeth (i.e., the two rows of teeth directly above the first row of teeth in FIG. 9) are offset or staggered relative to the teeth in the first row of teeth. In the illustrated embodiment, the teeth in the second and third rows of teeth are aligned with the gaps between the teeth in the first row. Additionally, the combined width of two teeth in the second and third rows is substantially equal to the widths of the gaps between the teeth in the first row (i.e., the teeth in the second and third rows cover the gaps between the teeth in the first row). Accordingly, together, the first, second, and third rows of teeth define a continuous cutting element (i.e., there are no gaps which extend through each of the first, second, and third rows of teeth). Thus, the teeth in the first, second, and third rows of teeth are configured to engage and cut the entire surface of the demineralized cortical bone strips. Otherwise, portions of the demineralized cortical bone strips corresponding to the positions of the gaps between the teeth would not be cut as the cylindrical drum rotates across the bottom surface of the cortical bone strip. In the illustrated embodiment, the fourth through eighth rows of teeth may be positioned the same or similar to the teeth in the first, second, and third rows of teeth, although the teeth in the fourth through eighth rows may be positioned differently than the teeth in the first, second, and third rows of teeth and still fall within the scope and spirit of the present disclosure.

Arranging the teeth on the cylindrical drum in a series of offset or staggered rows is configured to effectively and efficiently cut a high yield of elongated bone fibers from the cortical bone strips. Although the cylindrical drum in the illustrated embodiment includes eight rows of teeth, the cylindrical drum may have any other suitable number of rows of teeth, such as, for example, one to ten rows of teeth, and still fall within the scope and spirit of the present disclosure. For instance, the teeth may be arranged into four rows as described above with reference to FIG. 3. Additionally, the teeth may have any other suitable arrangement and still fall within the scope and spirit of the present disclosure. Moreover, although the teeth in the illustrated embodiment of FIG. 9 are rectangular, the teeth on the cylindrical drum may have any other suitable shape, such as semi-circular or triangular, and still fall within the scope and spirit of the present disclosure.

Figure 10:
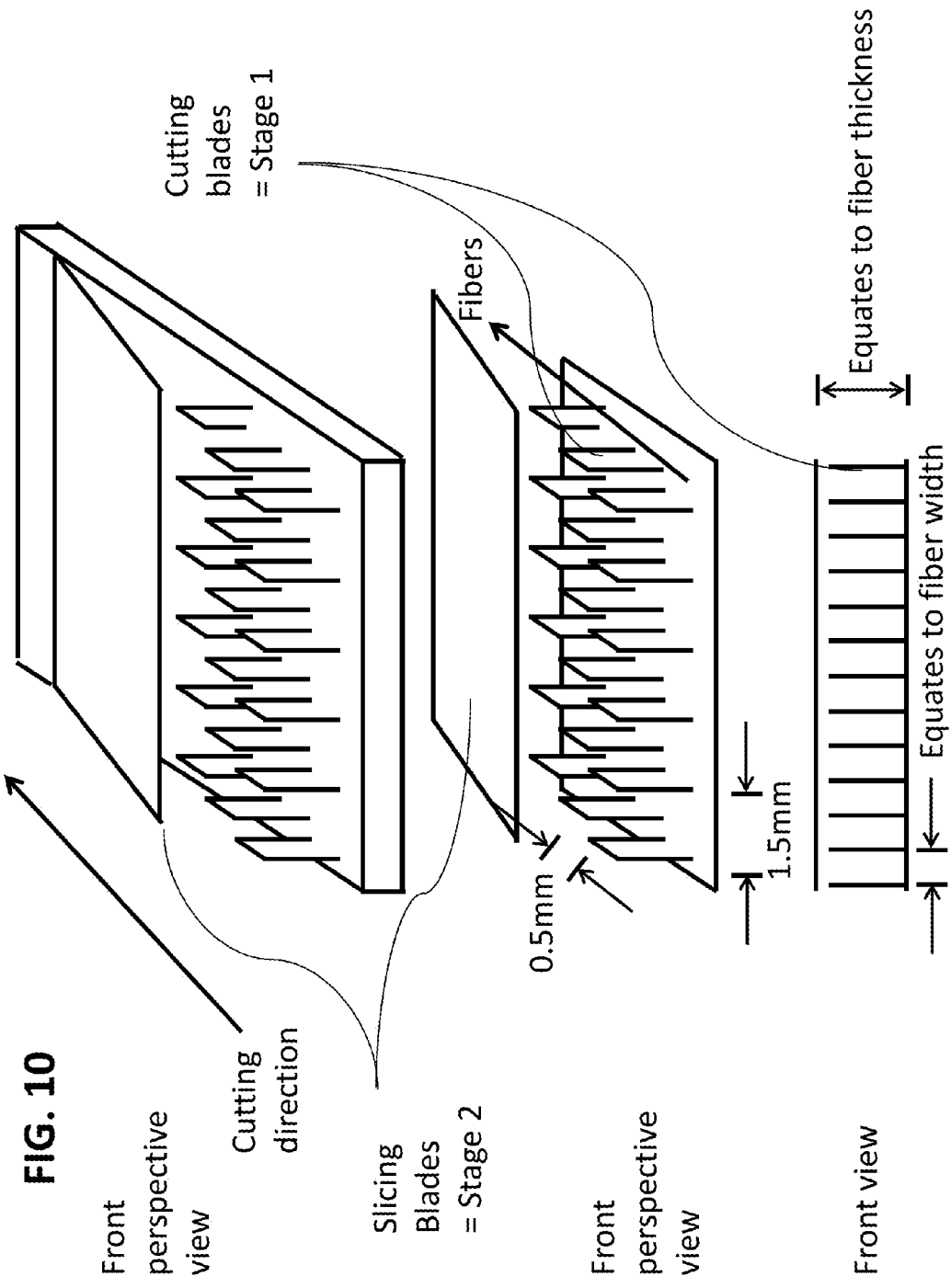
FIG. 10 is a schematic representation of a cutting device having two cutting surfaces, in which a first cutting stage (Stage 1) has cutting teeth/blades and a second cutting stage (Stage 2) has cutting blades, according to embodiments of the present invention.

With reference now to the embodiment illustrated in FIG. 10, a two-stage cutting device is illustrated. The two-stage cutting device may be incorporated into either the cutting assembly illustrated in FIG. 2 (i.e., the two-stage cutting device may replace the cutting element (50) or the cylindrical drum (90) illustrated in FIGS. 8A and 8B (i.e., the two-stage cutting device may be positioned on the outer surface of the cylindrical drum). The two-stage cutting device is configured to cut cortical bone strips into substantially uniform elongated bone fibers. In the illustrated embodiment, a first stage of the two-stage cutting device includes a plurality of thin teeth positioned along a support plate. The length of the teeth are oriented substantially parallel to the lengthwise direction of the cortical bone strips such that the teeth are configured to cut a series of narrow longitudinal grooves into the cortical bone strips. Additionally, the teeth are laterally spaced apart by gaps. The gaps between adjacent teeth define the spacing between adjacent longitudinal grooves in the cortical bone strips and the width of the elongated bone fibers which are subsequently cut from the cortical bone strips by a second stage of the two-stage cutting element. In the illustrated embodiment, the teeth are laterally spaced apart by approximately 0.5 mm, although the teeth may be spaced apart by any other suitable distance depending upon the intended use of the elongated bone fibers. Additionally, the teeth may have any suitable height, such as, for instance, approximately 0.2 mm to approximately 2 mm. The height of the teeth corresponds to the depth of the longitudinal grooves in the cortical bone strips and the thickness of the elongated bone fibers which are subsequently cut from the cortical bone strips by the second stage of the two-stage cutting element.

As illustrated in FIG. 10, the second stage of the two-stage cutting device includes a flat blade positioned above and behind the teeth on the first stage. The flat blade is positioned above and behind the teeth such that the teeth are configured to engage the cortical bone strips before the flat plate engages the bone strips. After the teeth have cut a series of narrow longitudinal grooves into the cortical bone strips, the flat blade of the second stage is configured to slice through the cortical bone strips to form the elongated bone fibers. As the flat blade slices through the cortical bone strips, the flat blade extends transversely between the longitudinal grooves, thereby cutting the elongated bone fibers from the cortical bone strips. It will be appreciated that the flat blade may cut through the cortical bone strips at a depth less than or substantially equal to the depth of the narrow longitudinal grooves in the bone strips formed by the teeth. Otherwise, the cortical bone strip would not separate into individual elongated bone fibers. Accordingly, the two-stage cutting device of the present disclosure is configured to produce a high yield of approximately uniform elongated fiber particles from the cortical bone strip. According to one embodiment, the yield of fibers from the cortical struts is at least 80% of the cortical strips.

Although in the illustrated embodiment of FIG. 10 the teeth of the first stage are rectangular, the teeth may have any other suitable shape, such as, for example, square or rounded. In another embodiment, the teeth of the first stage may be sharp pins or spikes. Additionally, as defined above, the teeth may be medium-sized or fine-sized, or any other suitable size depending upon the intended use of the elongated bone fibers. Moreover, the teeth of the first stage may have any suitable arrangement in addition to the arrangement depicted in FIG. 10.

Fixturing and cutting devices and mechanisms are depicted in FIGS. 2-10. The ability to efficiently fixture the demineralized cortical trips for cutting provides for elongated fibers having approximately uniform specifications. Fibers formed from one process according to embodiments of the present invention are at least 60% uniform. That is, in a batch of fibers formed from cortical strips following one process and one cutting device and mechanism at least 60% of the batch have approximately the same cross-sectional dimensions. In some embodiments at least 90% of the batch of fibers have approximately uniform cross-sectional dimensions.

Figure 11:
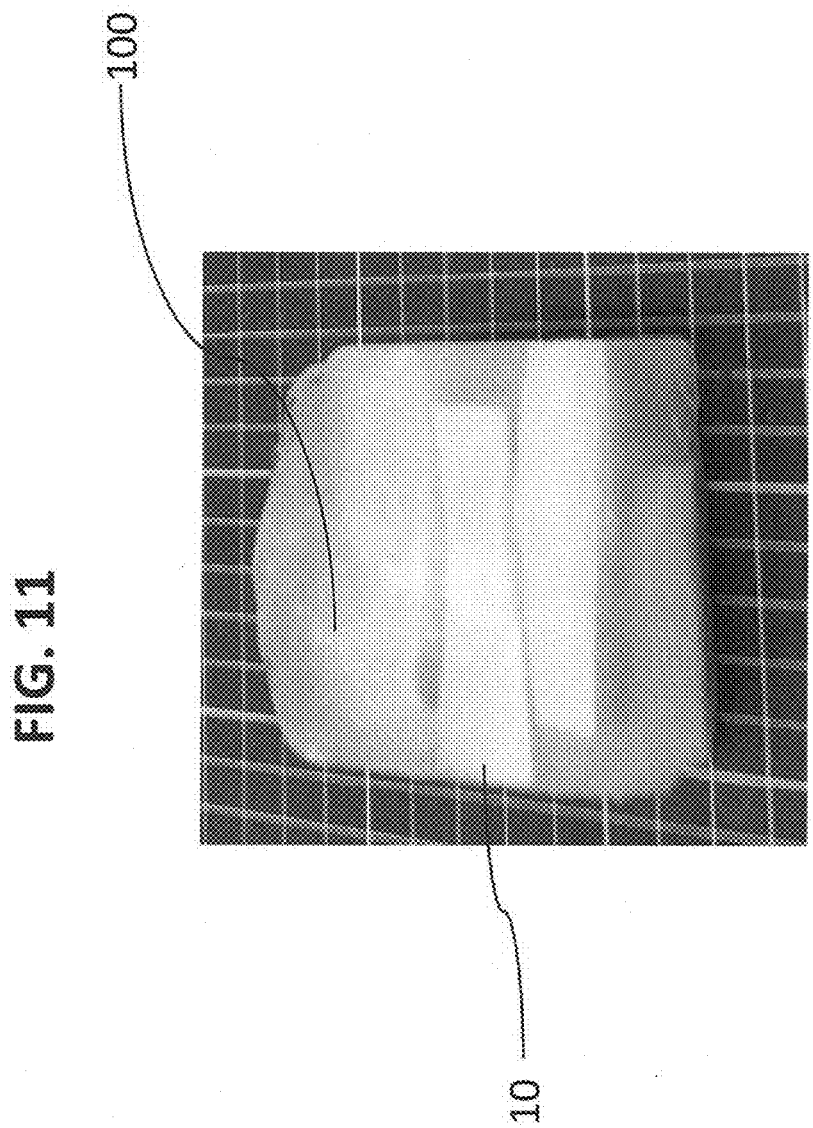
FIG. 11 is a photograph of bone cortical struts (10) aligned in an ice block (100), according to embodiments of the present invention.

In addition to the devices and methods discussed above in reference to FIGS. 2-10, in some embodiments of present invention, demineralized bone struts (10) are aligned in parallel in an aqueous solution and then frozen to form a uniform block of ice (100), as shown in FIG. 11. This method aligns the struts longitudinally so that when they are cut, the bone fibers are produced cutting along the orientation of the collagen fibers, i.e. along the long axis of the bone. This ice block method allows for the fixturing of multiple struts simultaneously, and for the fixturing of bone struts into a uniform dimension that is readily incorporated into a holding mechanism in a fiber cutting device. Additionally, the ice block method allows for reproducible cutting along the long axis, i.e. along the collagen fibers. The ice surrounding the bone strut or struts acts as a point of fixturing and obviates the need for an end of a bone strut to be held mechanically, thereby decreasing waste of the demineralized bone. Using the ice block method, the ice is removed along with the fibers as they are being cut. Cutting demineralized bone struts in an ice block does not affect the performance of the cutting operation, and adds lubricity as the ice is shaved and the water or saline melts. Any suitable aqueous solution may be used that is biocompatible and can be sterilized, for example, water, saline, and non-toxic solutions.

As mentioned, bone struts are more effectively and efficiently cut using the ice block method. For example, one donor may provide from 4 up to 8 bones. To obtain fiber lengths for use in the methods and compositions disclosed herein, the donated 4 to 8 bones may be cut into 3 inch width segments, which are then cut into half, for small bones, and cut into quarters for femurs and tibias. As such, one donor may produce 50-100 cortical struts. Using the ice block method, these 50 to 100 cortical struts are aligned and cut efficiently and effectively. Bone fibers were produced effectively using this method.

Processing of Fibers.

In some embodiments of the present invention, the cut demineralized bone fibers are collected for further processing. Processing of the fibers to produce a desired shape or form of the bone fibers may be performed using any suitable method. Examples of bone fiber products include, but are not limited to: a cavity, ball, pellet, sheet, strip, cylinder, cone, putty, gel, and injectable slurry. To make some of these forms, the bone fibers may be collected and compressed using pressure molds. In some embodiments, the bone fibers are formed using a wet lay technique as is well understood by those skilled in the art of nonwoven or paper manufacture, and described in "Nonwovens: Theory, Process, Performance, and Testing," 1993, Ed. A. Turbak, Chapter 6, ISBN: 089852265X; and Das et al., 2011, J. of Dispersion Sci and Technol., 33:1225-1232, the entire contents of all of which are herein incorporated by reference. Using a wet lay technique, the cut bone fibers are suspended in an aqueous solution to form a bone fiber slurry. Any suitable biocompatible aqueous solution may be used. Non-limiting examples of biocompatible aqueous solutions include: water, saline, and/or solutions including salts such as Ringer's solution, Lactated Ringer's solution, and saline with 5% dextrose. In some embodiments of the present invention, cut fibers are placed into saline to create a slurry of entangled bone fibers. The bone fiber slurry is suspended over a mesh screen and the saline is drained resulting in a wet lay process, such that a sheet of demineralized bone fibers is formed on the mesh screen. The thickness of the sheet depends on the amount of fibers and the size of the mesh screen. The resulting fiber sheet may be then dried using heat and/or vacuum or other means such as lyophilization (freeze-drying). In some embodiments, prior to drying, the sheet is placed in a mold and compressed to a defined thickness and shape, followed by drying. As discussed herein, density, porosity and overall dimensions of the resulting product may be controlled using various molds and techniques.

In some embodiments, the mesh screen is contoured to provide a three dimensional shape to the material.

In some embodiments, the formed wet lay fiber sheets may be placed into a vacuum oven and heated as a means to enhance cohesiveness of the bone fiber product. As used herein, "cohesive" and "cohesiveness" are used to refer to the integrity of the bone fiber products. That is, a cohesive bone fiber product stays together, does not fall apart and maintains its shape. As the bone fibers are in a hydrated state, heating to temperatures of about 30° to about 70° C. for about 30 minutes up to about 3 hours increases the cohesiveness by increasing the adherence of the collagen to other strands. In some embodiments, the heating temperature is about 45° to about 55° C. The application of vacuum removes moisture and dries the sheet.

In other embodiments, the bone fibers are further processed in a second drying step that may include vacuum drying and/or lyophilization.

In other embodiments the bone fibers may retain some moisture and will be placed in moisture impervious packaging.

The ability of the parameters of various stages of the above process to be modified allow for a broad range of products to be produced. A non-limiting range of bone fiber products includes sheets, strips, balls, cylinders, boats (e.g., cups), pellets, and cones, all of which may be used to bridge gaps and fill voids wherever bone formation is required. Example indications that may utilize such an implant product include spine, trauma, dental, craniofacial, and oral maxillofacial surgery.

In some embodiments, the elongated bone fiber particles may be formed into bone fiber balls that are readily rehydrated with blood, bone marrow aspirate, saline or other fluids and form a consistency of a malleable putty that readily conforms to a defect site yet avoids migration of the fibers. Bone fiber balls can also be readily mix with other graft materials including autologous bone (local bone or iliac crest bone), synthetic bone substitute materials, or with bone marrow aspirate harvested from the patient. When the fiber balls or fiber cubes are formed into a shape, for example, by hand, the resulting shape is maintained after it is placed onto a flat surface. That is, the ball does not flow or lose its shape, and it does not puddle. These integrity and consistency properties of the putty are useful for when the graft is placed into or onto a surgical site, the putty volume is maintained allowing for more robust bone formation. This integrity of the putty is in contrast to a form which could flatten and become thin such that bone formation would also be thin and less able to support weight or resist load. The bone fibers form a cohesive construct that resists migration compared to the small particles having a sand-like consistency used in conventional demineralized bone matrix powders. Small sand-like particles tend to lose their shape and migrate from the site.

In other embodiments, bone fiber forms made from the elongated bone fibers of the present invention include malleable putty, gel, and injectable forms. As used herein the term "putty" refers to a semi-solid composition made of a coherent mixture of at least elongated bone fibers that forms a soft, malleable, dough-like composition that does not flow and is capable of retaining its shape in the absence of any changes in applied force or temperature. The putty forms of currently available demineralized bone matrix (DBM) contain excipients to provide their consistency, whereas the presently disclosed putty is achievable without the need for any excipient by using elongate fibers that are entangled. The bone fibers may be dried, or produced in a hydrated state. While the putty does not require any liquid additives, it is also possible to make putties using bone fibers with excipients and/or additives.

In still other embodiments, the elongated bone fiber particles may be formed into a shape that provides a cavity (e.g., a boat, a cup, or a box). This cavity may be used to receive and incorporate an additive, for example, autologous bone chips, a morcellized autograft, bone marrow aspirate and/or other additives as described herein. The cavity shape allows the additive to be placed into the cavity area, and then the rehydrated bone fiber is kneaded around it forming a putty with the additive incorporated within the bone fibers of the cavity. This allows for the additive to be held together with the bone fibers and avoids migration of the additive from the site. The ability to form such a cohesive construct of demineralized bone fiber and additive is not easily achieved with known products and is an enhancement over current putty type products. Furthermore, to be able to achieve this without excipients is an improvement because excipients do not necessarily aid in bone healing, i.e. they may improve handling characteristics, but they may dilute the osteogenic material in the demineralized bone fiber.

In some embodiments, bone fiber pellets are formed by adding a wet fiber slurry into a cylindrical mold. An example of a cylindrical mold is a syringe. A bone fiber pellet shape is useful as it may be delivered to a graft site using a cannula as commonly used for minimally invasive surgery. The bone fiber pellets are capable of passing through a syringe barrel. A cylindrical mold is loaded with the fiber slurry and drained. In some embodiments, a fiber loaded cylindrical mold is dried by heat, vacuum, and/or lyophilization. After drying, the bone fiber pellet becomes more cohesive. After drying, the bone fiber pellets may be easily expelled out of the mold due to the shrinkage that occurs upon drying. The bone fiber pellets may be subsequently introduced into a liquid, such as water, saline, blood, and/or bone marrow aspirate, and they are readily rehydrated and expanded. After placement into surgical sites, rehydration occurs naturally due to the resident blood and moisture within the site. In some embodiments, one or more such bone fiber pellets may be utilized for minimally invasive grafting procedures such as spinal fusion, trauma and bone cysts as examples.

In some embodiments a sheet of elongated bone fibers is formed. As used herein, a "bone fiber sheet" may also be referred to as a "bone wrap," "bone paper," or "fiber wrap." The bone fiber sheet has utility in various applications, including trauma where they can be applied around fracture sites, as well as in dental applications where the bone wrap may be used for Guided Tissue Regeneration (GTR). In some embodiments, the bone fiber sheet has a thickness from about 0.5 to about 10 mm. The overall sheet size may be any size that is feasible for a bone repair application using a wet lay apparatus of a corresponding size. In some embodiments, the length and width of the bone fiber sheet are each independently from about 2 inches to about 8 inches. For example, the bone fiber sheet may be 2 inches by 4 inches, or the bone fiber sheet may be 4 inches by 4 inches. In another example, the bone fiber sheet may be 8 inches by 8 inches.

In some embodiments of the present invention, a bone fiber sheet has a side that is non-osteoinductive. Accordingly, a bone fiber sheet is formed using bone fibers that have been rendered non-osteoinductive by any suitable treatment, for example, by guanidine hydrochloride. The treated non-osteoinductive sheet is then placed on a second bone fiber sheet made from untreated fibers, and pressed together to form a sheet having different properties on each side. Heating this bone fiber sheet under light pressure at about 50° to about 55° C. will aid the cohesiveness of the sheet. Alternatively, a bone fiber sheet having a non-osteoinductive side and an osteoinductive side may be formed using a wet lay method in two stages with drying as described herein.

In some embodiments, a bone fiber sheet is made in a mold having raised areas such that when the mold is closed these areas become areas where the fiber becomes highly compressed, rendering a region having more dense bone fibers. When these areas are lines it produces strength in that direction, and a grid pattern produces strength in all directions. For example, the raised areas in the mold may be rods. The resulting grid or lined bone fiber sheet may be used as a sheet or dense bone fiber strips may be cut from the sheet.

In some embodiments, bone fibers are wet laid on to a surface that includes spikes projecting upward such that the fibers form a bone fiber sheet with the spikes projecting through the sheet. After heating and drying the spikes are removed leaving holes behind. The pattern of these spikes is designed to mimic the porosity of cancellous bone having a reproducibly defined pattern. In some embodiments, the spikes have a diameter of about 0.1 to about 1 mm and are arranged about 0.1 to about 2 mm apart, to form holes in the bone fiber sheet having corresponding diameters with corresponding spacing.

Alternatively, the bone fiber sheet is formed on a flat screen using standard wet lay methods. Spikes are then placed through the sheet to form the holes. After alternatively heating and drying, the spikes are removed leaving the holes in the bone fiber sheet.

The ability to control the porosity of the bone fiber sheets as described, allows for control of cellular ingrowth into the bone fibers. The ability to influence the biological response to the bone graft by controlling the porosity allows for a more effective composition for bone repair. Furthermore, a bone fiber composition prepared from cortical bone is more osteoinductive than demineralized cancellous bone.

While wet lay techniques are particularly good for the manufacture of different shapes from the bone fibers, it will be recognized that any other molding or forming technique used with textile fibers could be used. Fibers with and without excipients may be directly molded using compression into any shape.

The bone fiber composition of the present invention allows for the use of a wide range of bones including small bones like fibulae. Other processes such as those described in US Patent Publication Application No. 2008/0058953 are not practical with small bones as the force used during the milling operation breaks them resulting is significant waste. Utilization of small bones enhances the efficiency of the process, and also allows for production of fibers from small bones from other species such as canine, feline, etc. for use in veterinary bone repair.

Excipients and Additives.

The ability of the demineralized bone fiber products to mix with autograft bone, bone marrow aspirate and other materials improves the surgical utility of an implant made from the demineralized bone fibers of the present invention. Various aspects of product design including density, porosity, etc. influence the mixability and handling and may be incorporated into the design to maximize these properties. The ability to control the geometry of the demineralized bone fiber particles allows for tailoring the product for the indication.

In some embodiments of the present invention, incorporation of excipients may enhance handling properties of the bone graft. An excipient may be added to the bone material subsequent to demineralization. That is, an excipient may be added to the bone material before, after or concurrently with the bone cutting. Non-limiting examples of excipients that are also referred to as swelling agents include liquid polyhydroxy compounds and liquid polyhydroxy compound derivatives. The polyhydroxy compounds and derivatives of this type include those which in the pure or concentrated state and at ambient temperature are normally solid or semi-solid but are soluble in a suitable solvent, e.g., water, physiological saline, ethanol, glycerol, glucose, propylene glycol, polyethylene glycol of from 200-1000 molecular weight, etc., or mixtures thereof, to provide a liquid composition.

In particular, useful polyhydroxy swelling agents possess from 2 to about 18 carbons and include such classes of compounds as the acyclic polyhydric alcohols, non-reducing sugars, sugar alcohols, sugar acids, monosaccharides, disaccharides, water-soluble or water dispersible oligosaccharides, polysaccharides and known derivatives thereof. Specific polyhydroxy compounds include ethylene glycol, diethylene glycol, triethylene glycol, 1,2-propanediol, trimethylolethane, trimethylopropane, erythritol, pentaerythritol, polyalkylene glycols such as the polyethylene glycols, xylitol, sorbitol, mannitol, dulcitol, arabinose, xylose, ribose, adonitol, arabitol, rhamose, inositol, fructose, galactose, glucose, mannose, sorbose, sucrose, maltose, lactose, maltitol, lactitol, stachyose, maltopentaose, cyclomaltohexaose, trehalose, carrageenan, agar, alginic acid, guar gum, gum tragacanth, locust bean gum, gum arabic, xanthan gum, amylose, mixtures and copolymers thereof.

Derivatives of the polyhydroxy compounds, in particular, ester derivatives thereof, are also useful as swelling agents. For example, liquid and solid monoesters and diesters of glycerol can be used to good effect, the solid esters being dissolved up to the limit of their solubilities in a suitable vehicle, e.g., propylene glycol, glycerol, polyethylene glycol of 200-1000 molecular weight. Liquid glycerol esters include monacetin and diacetin and solid glycerol esters include such fatty acid monoesters of glycerol as glycerol monolaurate, glyceryl monopalmitate, glyceryl monostearate, etc. An example of a carrier herein comprises glyceryl monolaurate dissolved in glycerol or a 4:1 to 1:4 mixture of glycerol and propylene glycol.

In some embodiments, polyhydroxy excipients include glycerol and its liquid monoesters and diesters, e.g., monacetin and diacetin, fructose, trehalose, glucose and sucrose, and mixtures thereof. Where the polyhydroxy compound is a solid, e.g., sucrose, a solvent such as water, glycerol, polyethylene glycol of from 200-1000 average molecular weight, or mixture thereof is used to provide a flowable solution or bone fiber putty.

Additional non-limiting examples of suitable excipients include: lecithin, polyoxamer, hyaluronic acid, derivatized hyaluronic acids, and modified celluloses including carboxyl methyl cellulose and hydroxypropyl cellulose.

In some embodiments, a biocompatible material (an additive) is included to enhance the osteogenic properties of the bone implant. In some embodiments of the present invention, the bone fiber composition may also include an additive selected from bone marrow cells, mesenchymal stem cells, oxygenating materials (i.e., oxygen carrying materials), oxygen generating compounds, growth factors, antibiotics, antineoplastic agents, or combinations thereof. In some embodiments, the bone repair composition includes oxygenating materials such as a perfluorocarbon (PFC). In some embodiments, the repair composition includes oxygen generating compounds such as peroxides (e.g., hydrogen peroxide, calcium peroxide), perchlorates (e.g., sodium perchlorate, potassium perchlorate) percarbonates (e.g., sodium percarbonate), or perborates (e.g., sodium perborate).

The addition and selection of at least one biocompatible material may depend on the size of the bone graft site and the location of the site. Additional examples of biocompatible materials include: collagen and insoluble collagen derivatives, hydroxyapatite, tricalcium phosphate, and soluble solids and/or liquids dissolved therein, e.g., antiviricides, particularly those effective against HIV and hepatitis;

antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamycin; amino acids, magainins, peptides, vitamins, inorganic elements, co-factors for protein synthesis; hormones; endocrine tissue or tissue fragments; synthesizers; enzymes such as collagenase, peptidases, and oxidases; polymer cell scaffolds with parenchymal cells; surface cell antigen eliminators; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenic proteins (BMPs), transforming growth factor (TGF-beta), insulin-like growth factor (IGF-1); growth hormones such as somatotropin; bone digestors; antitumor agents; fibronectin; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; nucleic acids; and, bioerodable polymers such as those disclosed in U.S. Pat. Nos. 4,764,364 and 4,765,973 and European Patent Application 168,277. The amounts of such optionally added substances can vary widely with optimum levels being readily determined in a specific case by routine experimentation.

Other additives are contemplated to modify biological or other properties of the present invention. Non-limiting examples include growth factors such as bone morphogenetic proteins (BMPs), including BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, and BMP-18; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Osteoprotegerin, Transforming Growth Factor betas (TGF-.beta.s), including TGF-.beta.-1, TGF-.beta.-2, and TGF-.beta.-3, and inhibitors for tumor necrosis factor (e.g., anti-TNF.alpha.). Morphogens may also include Platelet Derived Growth Factors (PDGFs), including PDGF-A, PDGF-B, PDGF-C, PDGF-D, and GDF-5; rhGDF-5; and LIM mineralization protein, insulin-related growth factor-I (IGF-I), insulin-related growth factor-II (IGF-II), fibroblast growth factor (FGF) and beta-2-microglobulin (BDGF II), as disclosed in the U.S. Pat. No. 6,630,153, the entire contents of which are incorporated herein by reference. The polynucleotides encoding the same may also be administered as gene therapy agents. The preferred bioactive substances are the recombinant human bone morphogenetic proteins (rhBMPs) because they are available in relatively unlimited supply and do not transmit infectious diseases. In some embodiments, the bone morphogenetic protein is a rhBMP-2, rhBMP-4, rhBMP-7, or heterodimers thereof. BMPs are available from Wyeth, Madison, N.J., and may also be prepared by one skilled in the art as described in U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al., the entire contents of all of which are herein incorporated by reference.

EXAMPLES

The following examples use cortical bovine (cow) bone. As discussed herein, either human or animal bone may be used as a source of cortical bone.

Example 1

Demineralization

Cow bone was purchased that was a proximal tibia about 7 inches long. The metaphyseal portion above the flare was cut off using a power saw. The remaining shaft was then cut in half lengthwise, and the each half cut into longitudinal quarters. The resulting cortical struts were cleaned of adherent soft tissue and placed into a quart jar containing 0.6N HCl and allowed to sit at room temperature (63° F.) for 4 days. Modest bubbling was evident indicating the acid was reacting with the mineral component of the bone. After 4 days, the acid was replaced with fresh acid and the reaction was allowed to continue 3 more days. At this point the cortical struts had a rubbery feel and could be easily bent to 90° F. degrees, as shown in FIG. 1.

Bovine cortical rings were cut perpendicular to the long axis of the bone. The cortical rings were approximately ½ inch in thickness. Two rings were placed into each of 3 1-quart jars and the jars were filled with HCl of 6N, 3N and 0.6N. The rate of bubbling corresponded to the acid concentration, with bubbling most vigorous at 6N. The reaction was allowed to occur at room temperature for 3 hours at which time the bone in the 6N acid had lost diameter and appeared degraded. Upon handling, this specimen surprisingly was hard with a core of mineral in the center. It appears that 6N HCl has a destructive effect on the collagen under the conditions of this experiment.

Cow femur bone was cut into 3 inch segments and then split into quarters. This resulted in segments that were about 2 to 3 cm wide and 1 to 1.5 cm thick. When placed into an acid bath of 0.6N HCl at 1 gm bone to 20 mls of acid demineralization began as evidenced by mild bubbling. It was observed that about 2 mm of demineralization occurred every two days. As such, about 7 days were required to achieve complete demineralization in 0.6 N HCl.

Demineralization was carried out on cortical struts at concentrations from 1N to 6N hydrochloric acid (HCl). Cortical struts were placed into 1N, 3N, and 6N HCl. There was visible bubbling correlating with the acid concentration, i.e. the high acid had greater bubbling. After 3 hours at room temperature the bone in the 6N acid degraded. The 3N samples also appeared degraded yet still had obvious calcium within the center. The 1N HCl samples did not appear degraded, and were fully demineralized. The acid concentration for demineralization may be up to, but not more than 3N at a temperature up to 40° C.

Example 2

Cutting/Grater Blades

Figure 12:
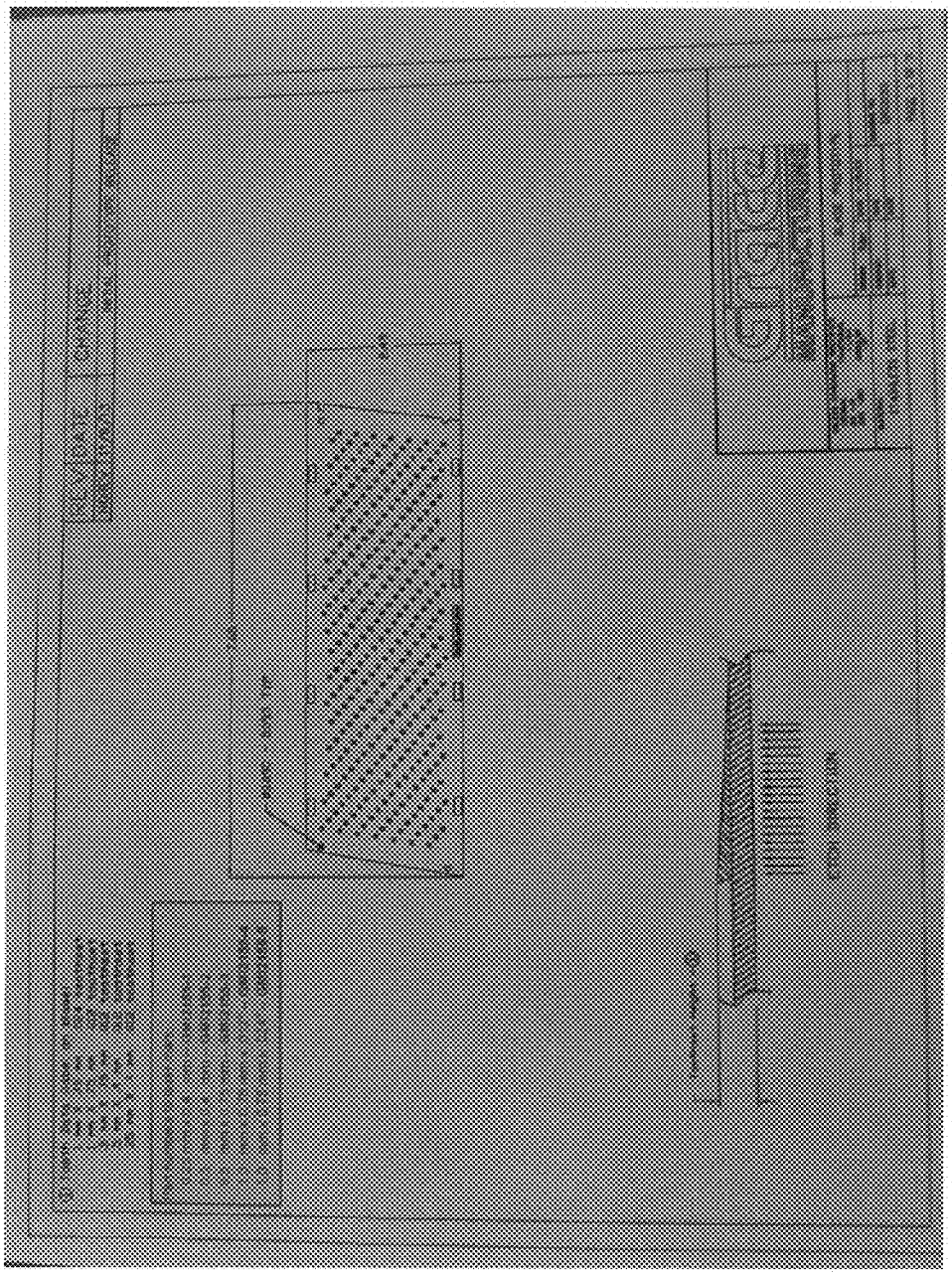
FIG. 12 is a photograph of the specifications for each of cutting blades 1, 2, 3, 4, and 5, according to embodiments of the present invention.
Figure 13:
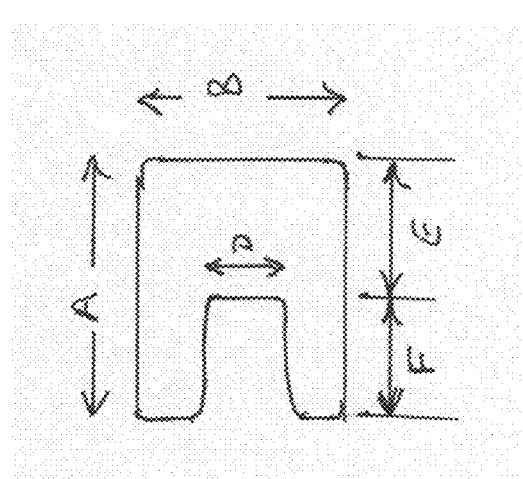
FIG. 13 is a schematic showing the dimensions A, B, D, E, and F, for each tooth of a cutting blade, according to embodiments of the present invention.

Fiber grater blades were obtained from Grace Manufacturing with 5 different cutting geometries. The tooth design of each grater is illustrated in FIGS. 12 and 13 and detailed below with measured dimensions A, B, D, E, and F as indicated in FIG. 13.

TABLE 1

| Blade | A | B | D | E | F |
|---|---|---|---|---|---|
| 1 | 1.36 | 0.75 | 0.27 | 0.55 | 0.68 |
| 2 | 1.38 | 1.02 | 0.27 | 0.65 | 0.67 |
| 3 | 1.41 | 1.28 | 0.3 | 0.74 | 0.67 |
| 4 | 1.91 | 1.7 | 0.82 | 1.09 | 0.76 |
| 5 | 1.93 | 1.61 | 0.64 | 1.09 | 0.84 |

Figure 14:
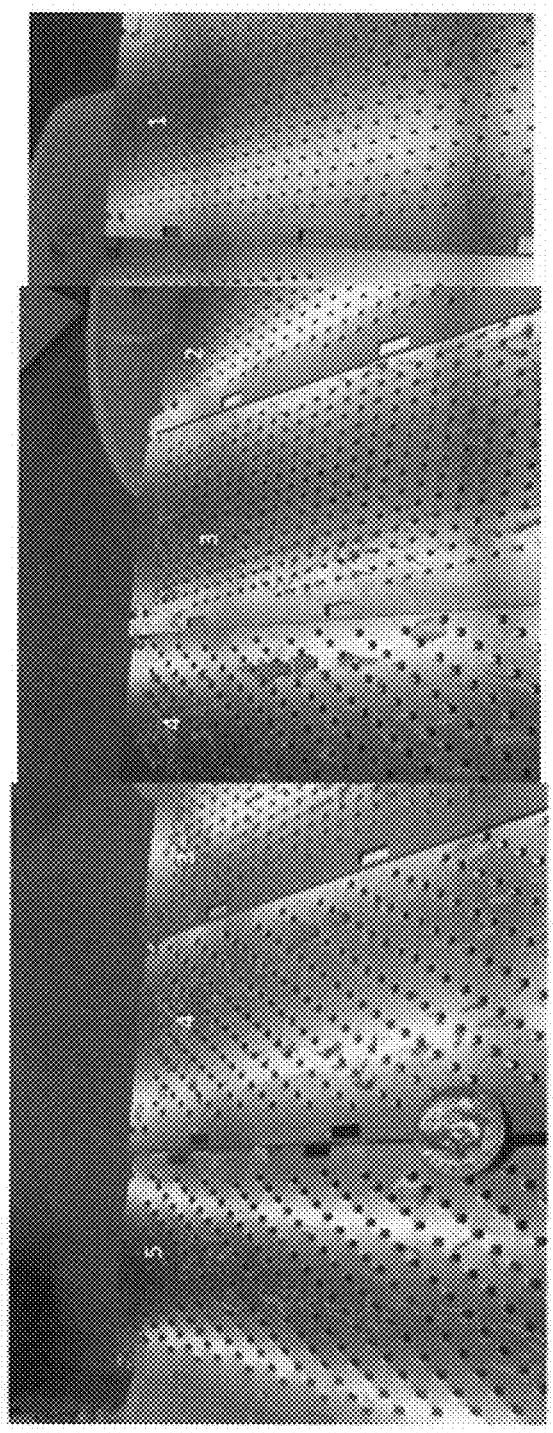
FIG. 14 is a photograph of each of cutting blades 1, 2, 3, 4, and 5, according to embodiments of the present invention.
Figure 15A:
FIG. 15A is a photograph of elongated bone fibers cut from cutting blades 1, 3, 5, and 4, respectively, in clockwise order starting at the bottom right corner, according to embodiments of the present invention.
Figure 15B:
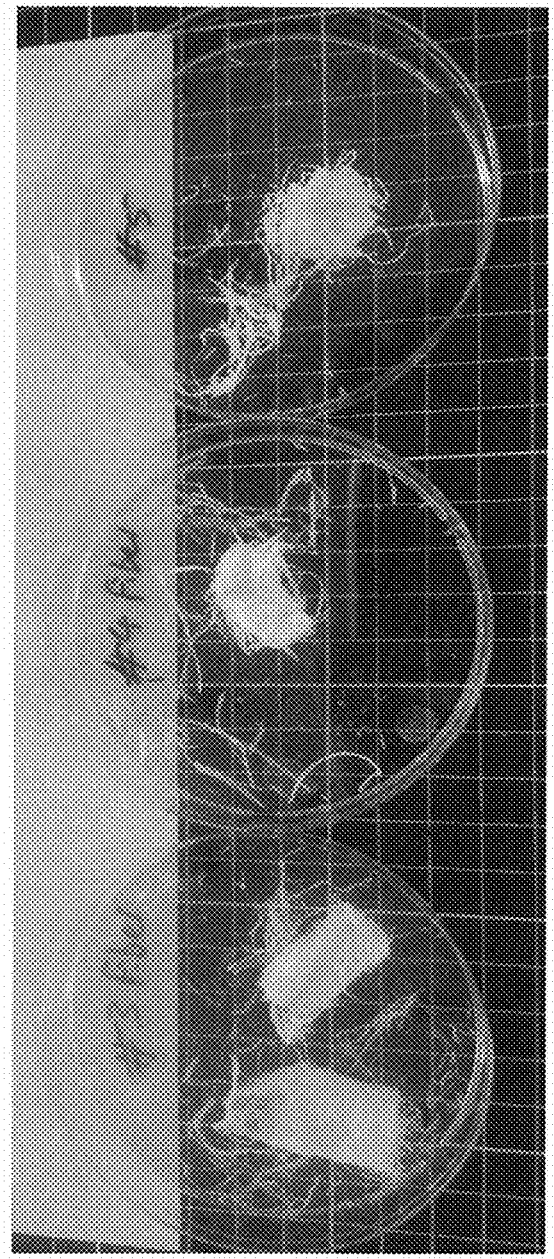
FIG. 15B is a photograph of elongated bone fibers cut from cutting blades 3, 4, and 5, respectively, from left to right, according to embodiments of the present invention.

Using the various sized blades 1, 2, 3, 4, and 5 as shown in FIG. 14, various sized fibers were produced from demineralized cortical struts of Example 1, as shown in FIGS. 15A and 15B. In this way, a selected geometry may be more efficiently and effectively produced using an optimal blade size. For example, fibers from blades 4 and 5 may be suitable for large fiber strips, while fibers from blades 3 and 4 may be a more optimal size for smaller strips, fiber balls and/or fiber putty. Additionally, fibers from blades 2 and/or 3 may be more optimal for bone wrap (paper).

For improved use of the grater blade, the blade was incorporated into a plastic frame including a handle, as shown in FIGS. 16A and 16B. In some embodiments, the grater blades may be attached to an automated machine that allows for increased production. An automated machine actuates movement of the blade while retaining the demineralized cortical bone strut or struts. Various aspects of an automated cutting device machine are shown in FIGS. 2A and 2B, 6a, 6B, and 7 as described herein.

Example 3

Bone Fiber Putty

Bone fibers produced using demineralized bovine bone and cut with a #4 blade were lightly squeezed between non-linting, non-woven absorbent paper to remove excess water. 4.75 g of the bone fibers were placed in a 15 ml Nalgene jar. The product was a conformable "putty" type of product that could be easily molded by hand. The product filled the jar and so the density of the putty was approximately 0.3 g/ml. It was also able to absorb blood.

Bone fibers produced using demineralized bovine bone cut with a #3 blade were lightly squeezed between non-linting, non-woven absorbent paper to remove excess water. 4.02 g of the bone fibers were placed in a 15 ml Nalgene jar. The product was a conformable "putty" type of product that could be easily molded by hand. The product filled the jar and so the density of the putty was approximately 0.3 g/ml. It was also able to absorb blood. In comparison to the putty product cut with the #4 blade, the finer fibers cut with the #3 blade were easier to handle as a putty.

Bone fibers produced using demineralized bovine bone cut with a #4 blade were lightly squeezed between non-linting, non-woven absorbent paper to remove excess water. 4.75 g of the bone fibers were placed in a 15 ml Nalgene jar. 3 g of glycerol (Sigma) was added to the bone fibers in the jar and mixed using a spatula. The product was allowed to equilibrate overnight. The product was a conformable "putty" type of product that was easily molded by hand. The putty did not completely fill the jar and so the density was greater than in the example without excipient above.

Bone fibers produced using demineralized bovine bone cut with a #3 blade were lightly squeezed between non-linting non-woven absorbent paper to remove excess water. 4.02 g of the bone fibers were placed in a 15 ml Nalgene jar. 2.57 g of glycerol (Sigma) was added to the fibers in the jar and mixed using a spatula. The product was allowed to equilibrate overnight. The product was a conformable "putty" type of product that could be easily molded by hand. The putty did not completely fill the jar and so the density was greater than in the example without excipient above. In comparison to the glycerol putty product cut with the #4 blade, the finer fibers cut with the #3 blade were easier to handle as a putty with few fibers falling out of the putty composition.

Example 4

Bone Fiber Strips

Figure 17B:
FIG. 17B is a photograph of the sheet mold of FIG. 17A with a compressed bone fiber sheet in the bottom tray, according to embodiments of the present invention.
Figure 17A:
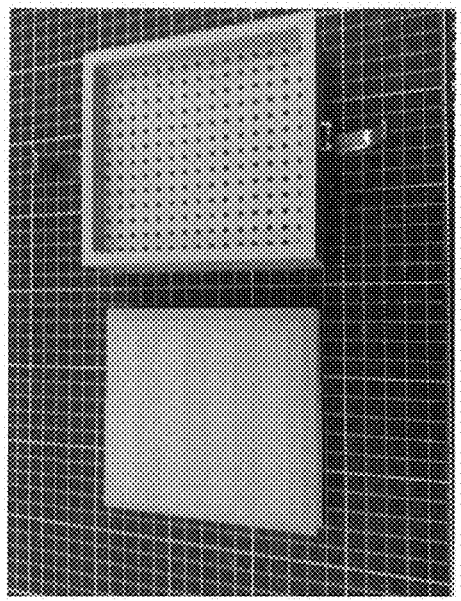
FIG. 17A is a photograph of a sheet mold with a lid (left) having raised regions to form troughs in the bone fiber sheet, and a bottom tray (right) with holes for drainage, according to embodiments of the present invention.
Figure 17C:
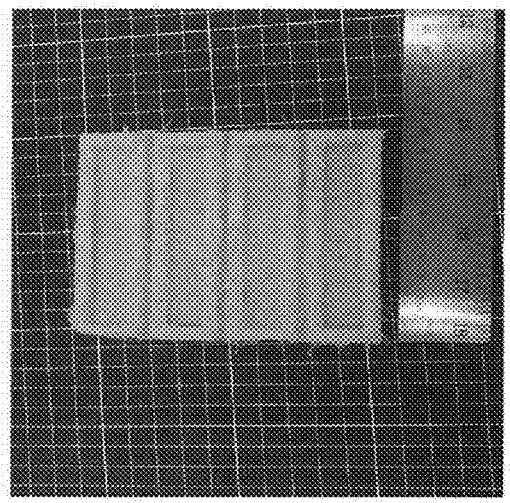
FIG. 17C is a photograph of the bone fiber sheet having strips with troughs made by the sheet mold of FIGS. 17A, 17B, according to embodiments of the present invention.

Demineralized bone fiber strips were produced using hand molds and wet-laying. In brief, wet-laying includes adding saline into a wet lay apparatus having a screen filter. The cut bone fibers are suspended in a solution to form a slurry, which is poured onto the screen. In this example, wet lay sheets of fiber were produced using a wet lay apparatus vessel having a 4 inch by 4 inch screen. Approximately 50 grams of fibers were suspended in saline and poured into the apparatus. The slurry and saline were stirred to maintain a uniform dispersion of fibers, and then the slurry liquid is drained through drain valve in the wet lay apparatus, resulting in the fibers collecting as a uniform sheet on the screen within the apparatus. This fiber sheet was then transferred to a sheet mold (FIG. 17A) in which the lid (left image in FIG. 17A) has raised regions that form indents or troughs in the fiber. The holes in the bottom holding tray (right image in FIG. 17B) allow excess liquid to egress during compression and drying when the lid is in place. The loaded and fitted mold was placed into a heating oven and warmed to 50-55° C. for about 1 hour. This heating step enhanced the cohesiveness of the strips. The resulting fiber strips having a molded trough region are shown in FIG. 17B and were removed from the mold (FIG. 17C). As shown (FIGS. 17B, 17C), the 4 inch×4 inch mold makes 4 strips that are 2.5 cm×10 cm×6 mm thick with a region in the center that is 4 mm deep to provide a trough for placing autograft or other graft materials. This region is 5 mm from the sides. The indents between the strips mark where the sheet can be cut to separate the sheet into individual strips.

An additional sheet mold was used having a lid with raised regions that formed trough regions in the fiber strip having a depth of both 1 and 2 mm and slopes on the sides of the strips at angles of 45° and 25°. The sloped sides of the fiber strip mold keeps the edges of the fiber strip more uniform. Additionally, the resulting fiber strips having decreased trough depths provide an increase in the overall porosity of the fiber strip.

Example 5

Bone Fiber Strips with Autograft

Figure 18A:
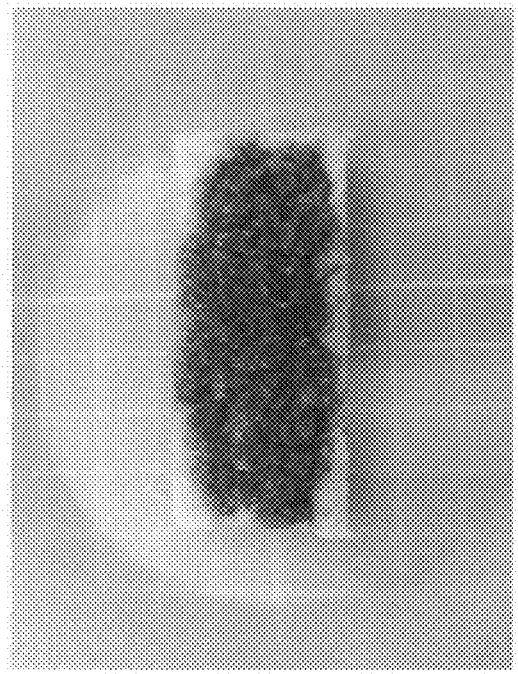
FIG. 18A is a photograph of a top view of a bone fiber strip having a trough region incorporated with an autograft of sheep blood and cancellous bone chips, according to embodiments of the present invention.
Figure 18B:
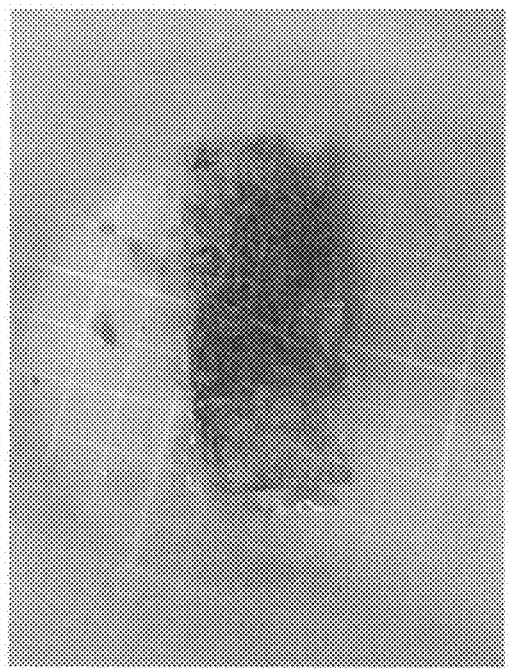
FIG. 18B is a photograph of bottom view of the bone fiber strip of FIG. 18A showing absorption of blood through to the underside, according to embodiments of the present invention.

An autograft was applied to the trough region of the fiber strips of Example 4. The autograft surrogate was made by combining sheep blood with cancellous chips of bone crushed to approximately 2-3 mm in size. Upon application to the fiber strip, the blood readily wicked into the fiber matrix of the strip (FIG. 18A). When the strip was inverted the autograft surrogate remained in place and the bottom of the strip (FIG. 18B) was red, indicating the blood readily absorbed into and wicked through the matrix.

Example 6

Bone Fiber Shapes

Figure 19:
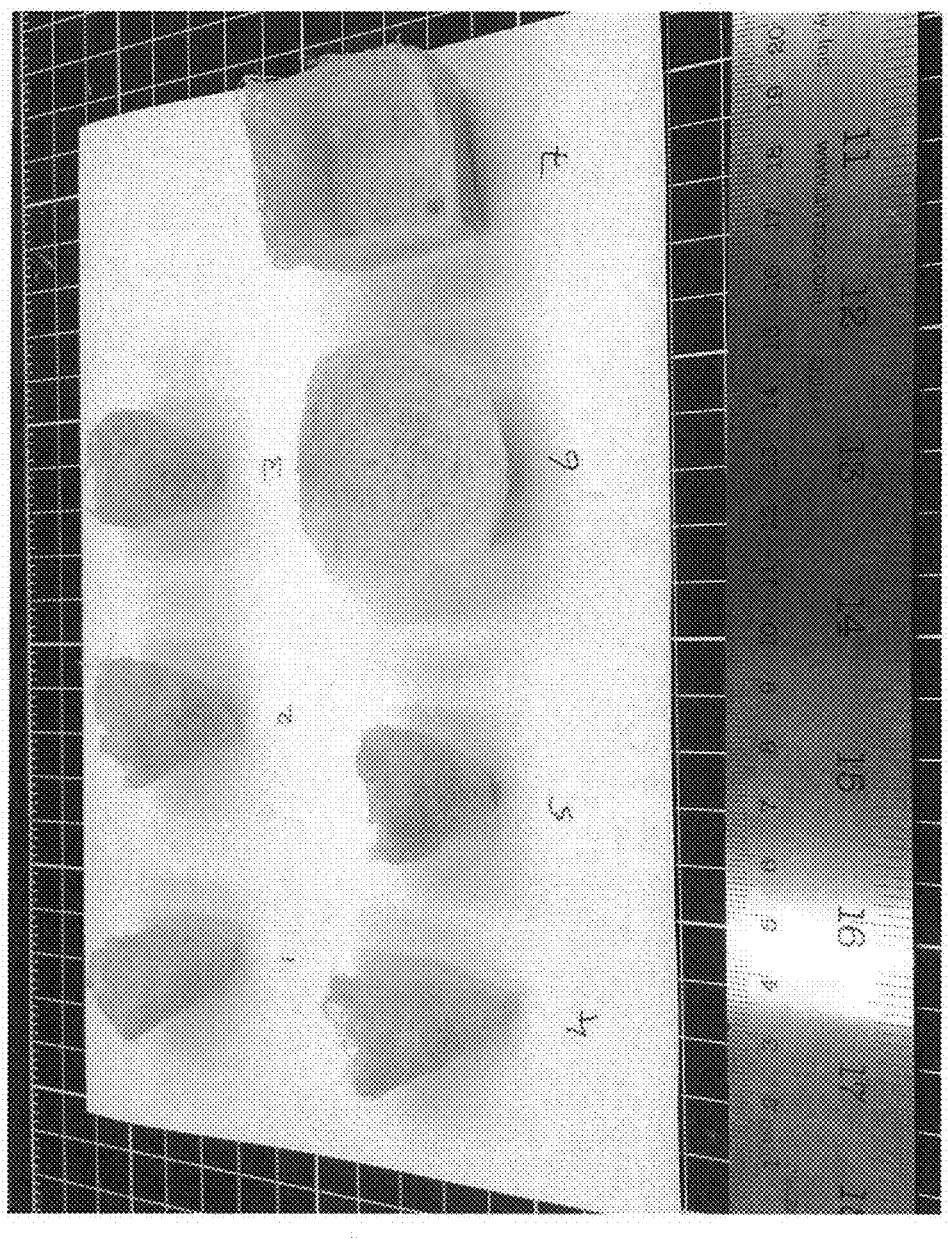
FIG. 19 is a photograph of bone fiber cups (1-5), a bone fiber ball (6), and a bone fiber box (7), as indicated, according to embodiments of the present invention.

Cups, Balls, Box. The bone fiber shapes 1-7 as shown and indicated in FIG. 18 were made using a wet lay technique as described in Example 3. The fiber cups 1-5 as shown in FIG. 9 were formed using a wet lay screen having the same shape as the product shape. The fiber ball shape 6 as shown in FIG. 19 was formed using half of a screen tea ball as a mold. The fiber box 7 was made from a custom screen having the same box shape.

Example 7

Bone Fiber Pellets

Figure 20:
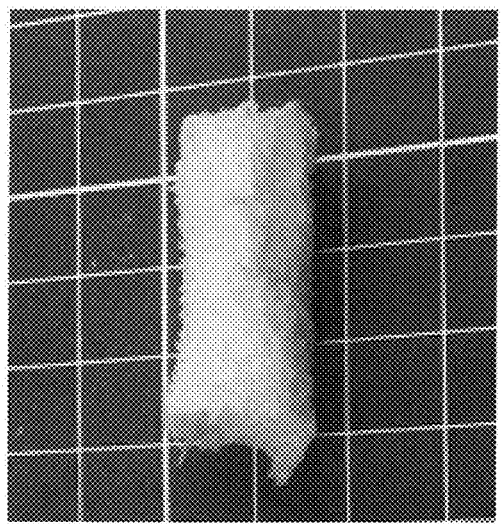
FIG. 20 is a photograph of a bone fiber pellet made from a 10 cc syringe, according to embodiments of the present invention.

Bone fiber pellets were formed by placing wet fibers in a slurry into 1, 3, and 10 cc (cubic centimeter) syringes and then inserting the plunger and forcing out moisture and compacting the fibers. The Luer lock end of the syringe was removed and the resulting pellet-shaped fiber form was expelled from the syringe. The entangled mass of fibers formed a coherent pellet of a diameter commensurate with the 10 cc syringe size as shown in FIG. 20). In some examples, after removing the Luer end, the fiber loaded syringes were placed into a convection oven at 50° C. for 1 hour to enhance cohesiveness of the fibers. In other examples, after heating at 50° C. for 1 hour, fiber loaded syringes were placed into a vacuum oven overnight to remove moisture. This resulted in shrinkage of the 'fiber pellet' to about 50% of the original diameter. In all of these examples the pellets were cohesive, with increased cohesion observed after heating.

Example 7

Bone Fiber Sheet

Figure 21:
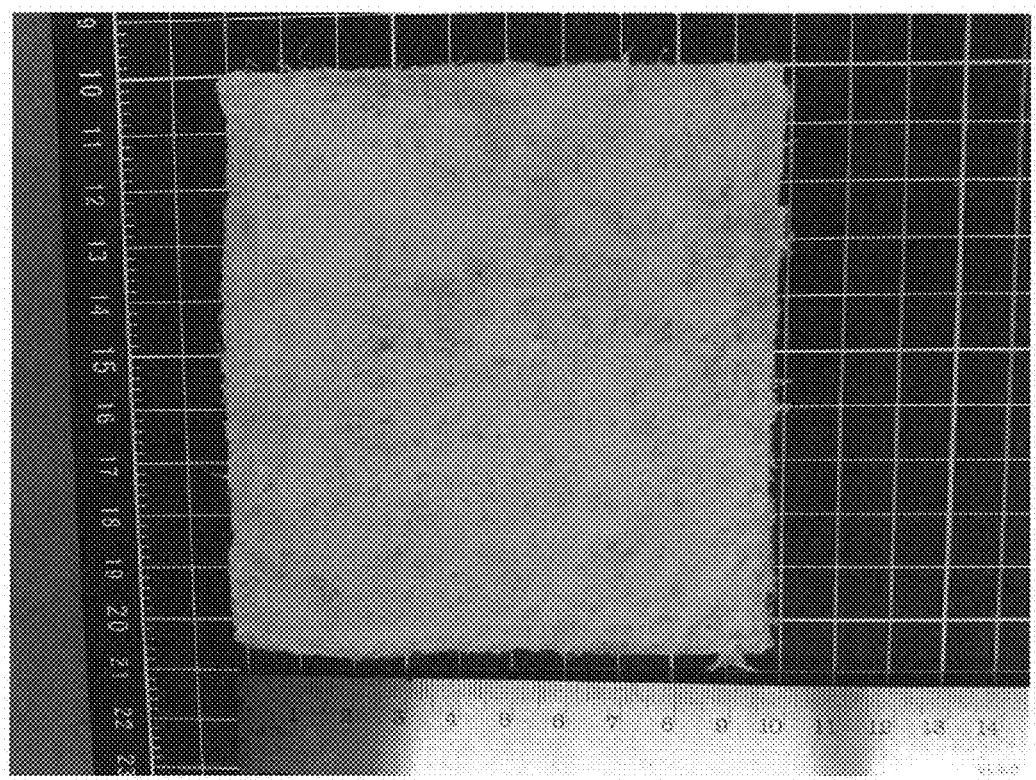
FIG. 21 is a photograph of a 1 mm thick, 4 inch by 4 inch bone fiber sheet made according to embodiments of the present invention.

A 1 mm thick sheet of bone fiber sheet was made as shown in FIG. 21. This bone fiber sheet was made using the wet lay technique as described in Example 3, except 15 grams of fibers were suspended in a saline slurry and added to a wet lay apparatus having a 4 inch by 4 inch screen. The sheet of bone on the wet lay screen was removed and placed into a mold that pressed the sheet to a thickness of about 1 mm, and then was heated at 50° C. for about an hour with a compression weight placed on top of the fiber sheet.

Example 8

Demineralized Bone Fibers with Oxygen Generating Compound

A slurry of demineralized bone fibers further including calcium peroxide as an oxygen generating compound was created using the following ratios: 1 cc PFTBA (perfluoro tributylamine), 1 cc 20% Pluronic® F68, 1 cc lecithin, and 250 mg $CaCO_2$ was mixed to create a low viscosity slurry. The slurry was wet laid into a sheet as in Examples above, followed by drying of the sheet using vacuum oven at 40° C. The resulting fiber sheet was compressible. The removal of water using this method stabilized the $CaO_2$ as water is required for the oxygen releasing reaction to appreciably occur.

As shown in the present Examples and FIGS. 1-21, elongated bone fibers made using methods as disclosed herein, allow for bone fiber compositions having controlled and uniform geometries. This controlled geometry allows for uniformity amongst the individual bone fibers and reproducible bone implants made from the elongated fiber fibers, as well as an increase in the amount of useable bone material.

While the present invention has been illustrated and described with reference to certain exemplary embodiments, those of ordinary skill in the art will understand that various modifications and changes may be made to the described embodiments without departing from the spirit and scope of the present invention, as defined in the following claims. Additionally, although relative terms such as "outer," "inner," "upper," "lower," "below," "above," "vertical, "horizontal" and similar terms have been used herein to describe a spatial relationship of one element to another, it is understood that these terms are intended to encompass different orientations of the various elements and components of the device in addition to the orientation depicted in the figures.

What is claimed is:

1. A method of producing a bone composition comprising a plurality of demineralized elongated bone fibers having approximately uniform geometry, the method, comprising:
   cutting cortical bone into struts;
   demineralizing the cortical bone struts to form demineralized bone having a calcium content of no more than 10%;
   fixturing the demineralized cortical struts to a cutting apparatus with collagen fibers of the demineralized cortical struts aligned parallel to a cutting direction of the cutting apparatus; and
   repeatedly cutting the demineralized bone to form the plurality of demineralized elongated bone fibers having a length from about 1 cm to about 30 cm.

2. The method of claim 1, wherein the demineralization comprises soaking the bone in a dilute acid having a concentration of about 0.3 N to about 3 N.

3. The method of claim 1, further comprising:
   rinsing the demineralized bone to form a rinsed demineralized bone; and
   freezing the rinsed demineralized bone.

4. The method of claim 1, further comprising adding an excipient and/or an additive to the demineralized elongated bone fibers.

5. The method of claim 1, wherein of the plurality of elongated bone fibers, at least 60% are approximately uniform within one standard deviation.

6. The method of claim 1, wherein the plurality of elongated bone fibers are formed into a cavity, ball, pellet, wrap, strip, cylinder, cone, putty, gel, and injectable slurry.

7. The method of claim 1, the method further comprising:
   suspending the plurality of elongated bone fibers in an aqueous solution to form a suspension of elongated bone fibers;
   adding the suspension of elongated bone fibers to a mold to form a mold of elongated bone fibers; and
   draining the suspension of the aqueous solution from the mold of elongated bone fibers.

8. The method of claim 7, further comprising:
   compressing the elongated bone fibers in the mold.

9. The method of claim 8, wherein the mold comprises raised areas and the compressing of the elongated bone fibers comprises more compression along the elongated bone fibers corresponding to the raised areas of the mold relative to the elongated bone fibers.

10. The method of claim 7, further comprising:
heating the mold of elongated bone fibers.

11. The method of claim 7, further comprising:
drying the mold of elongated bone fibers.

12. The method of claim 11, wherein the drying comprises heating, vacuum, and/or lyophilization.

13. The method of claim 7, wherein the mold is cylindrical and forms a cylindrical shape of elongated bone fibers.

14. The method of claim 13, further comprising loading the cylindrical shape of elongated bone fibers into a cannula.

15. The method of claim 7, wherein the plurality of elongated bone fibers comprises a first group of bone fibers and a second group of bone fibers, wherein the first group is treated to remove osteoinductive matter to form a treated group of bone fibers and the second group is an untreated group of bone fibers, and the treated group of bone fibers and the untreated group of bone fibers are added to the mold to form elongated bone fibers having at least one osteoinductive region and at least one non-osteoinductive region.

16. The method of claim 2, wherein the dilute acid has a concentration of about 0.3 N to about 0.6 N.

17. The method of claim 1, wherein the struts have a maximum thickness of 8 mm.

* * * * *